United States Patent
Lossos et al.

(10) Patent No.: US 9,447,160 B2
(45) Date of Patent: Sep. 20, 2016

(54) COMPOSITIONS, METHODS AND KITS FOR TREATMENT OF CANCER AND AUTOIMMUNE DISEASES

(71) Applicant: UNIVERSITY OF MIAMI, Miami, FL (US)

(72) Inventors: Izidore Lossos, Miami, FL (US); Shruti Bhatt, Miami, FL (US); Joseph Rosenblatt, Hollywood, FL (US); Seung-Uon Shin, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 14/373,137

(22) PCT Filed: Jan. 18, 2013

(86) PCT No.: PCT/US2013/022164
§ 371 (c)(1),
(2) Date: Jul. 18, 2014

(87) PCT Pub. No.: WO2013/109904
PCT Pub. Date: Jul. 25, 2013

(65) Prior Publication Data
US 2015/0044134 A1 Feb. 12, 2015

Related U.S. Application Data

(60) Provisional application No. 61/588,486, filed on Jan. 19, 2012.

(51) Int. Cl.
| | | |
|---|---|---|
| *A61K 38/00* | (2006.01) | |
| *C07K 16/00* | (2006.01) | |
| *C07K 14/55* | (2006.01) | |
| *C07K 14/54* | (2006.01) | |
| *C07K 16/28* | (2006.01) | |
| *A61K 38/20* | (2006.01) | |
| *A61K 39/395* | (2006.01) | |
| *A61K 45/06* | (2006.01) | |
| *A61K 51/00* | (2006.01) | |
| *A61K 39/00* | (2006.01) | |

(52) U.S. Cl.
CPC .......... *C07K 14/55* (2013.01); *A61K 38/2013* (2013.01); *A61K 39/39558* (2013.01); *A61K 45/06* (2013.01); *A61K 51/00* (2013.01); *C07K 14/54* (2013.01); *C07K 16/2887* (2013.01); *A61K 38/00* (2013.01); *A61K 2039/505* (2013.01); *C07K 2317/54* (2013.01); *C07K 2317/55* (2013.01); *C07K 2317/73* (2013.01); *C07K 2317/732* (2013.01); *C07K 2317/76* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 6,111,093 A | 8/2000 | Seed et al. | |
| 7,807,409 B2 * | 10/2010 | Kopetzki | 435/69.1 |
| 7,919,273 B2 | 4/2011 | Goldenberg et al. | |
| 8,057,793 B2 * | 11/2011 | Hansen et al. | 424/133.1 |
| 2005/0265966 A1 * | 12/2005 | Kindsvogel | A61K 38/20 424/85.2 |
| 2010/0330089 A1 * | 12/2010 | Damle | C07K 16/2887 424/135.1 |

FOREIGN PATENT DOCUMENTS

| | | |
|---|---|---|
| WO | WO-2007/045465 A1 | 4/2007 |
| WO | WO-2010/124361 A1 | 11/2010 |
| WO | WO 2010124361 A1 * | 11/2010 |

OTHER PUBLICATIONS

Gelebart et al., Interleukin-21 effectively induces apoptosis in mantle cell lymphoma through a STAT1-dependent mechanism, Leukemia, 23(10):1836-46 (2009).
International Preliminary Report on Patentability, corresponding international application No. PCT/US13/22164 (Jul. 22, 2014).
International Search Report and Written Opinion, corresponding international application No. PCT/US13/22164 (mailing date Apr. 30, 2013).
Sarosiek et al., Novel IL-21 signaling pathway up-regulates c-Myc and induces apoptosis of diffuse large B-cell lymphomas, Blood, 115(3):570-80 (2010).

* cited by examiner

*Primary Examiner* — Jeanette Lieb
(74) *Attorney, Agent, or Firm* — Marshall, Gerstein & Borun LLP

(57) ABSTRACT

The present invention is directed to fusion proteins having an IL-21 cytokine portion and an anti-CD20 antibody portion, and methods of using such fusion proteins. The invention also provides pharmaceutical compositions and kits utilizing the IL-21-anti-CD20 fusion proteins. In particular, the methods, kits and compositions of the invention are useful in the treatment of cancer and autoimmune diseases.

32 Claims, 15 Drawing Sheets

SEQUENCE LISTING

<160> NUMBER OF SEQ ID NOS: 14

<210> SEQ ID NO 1
<211> LENGTH: 15
<212> TYPE: PRT
<213> ORGANISM: Homo sapiens

<400> SEQUENCE: 1

Ser Gly Gly Gly Gly Ser Gly Gly Gly Ser Gly Gly Gly Gly
1               5                   10                  15

<210> SEQ ID NO 2
<211> LENGTH: 8
<212> TYPE: PRT
<213> ORGANISM: Homo sapiens

<400> SEQUENCE: 2

Ile Pro Ala Gly Ile Tyr Pro Ile
1               5

<210> SEQ ID NO 3
<211> LENGTH: 16
<212> TYPE: PRT
<213> ORGANISM: Homo sapiens

<400> SEQUENCE: 3

His Phe Leu Lys Met Glu Ser Leu Asn Phe Ile Arg Ala His Thr Pro
1               5                   10                  15

<210> SEQ ID NO 4
<211> LENGTH: 297
<212> TYPE: PRT
<213> ORGANISM: Homo sapiens

<400> SEQUENCE: 4

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
        210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Gly Pro Pro Gln Asp Gln Glu Ser
        275                 280                 285

Ser Pro Ile Glu Asn Asp Ser Ser Pro
    290                 295

<210> SEQ ID NO 5
<211> LENGTH: 39
<212> TYPE: DNA
<213> ORGANISM: Homo sapiens

<400> SEQUENCE: 5
ggggatatcc accatggrat gsagctgkgt matsctctt                              39

<210> SEQ ID NO 6
<211> LENGTH: 39
<212> TYPE: DNA
<213> ORGANISM: Homo sapiens

<400> SEQUENCE: 6
aggtctagaa yctccacaca caggrrccag tggatagac                              39

<210> SEQ ID NO 7
<211> LENGTH: 39
<212> TYPE: DNA
<213> ORGANISM: Homo sapiens

<400> SEQUENCE: 7
ggggatatcc accatggaat ggagctgggt aatcctctt                              39

<210> SEQ ID NO 8
<211> LENGTH: 28
<212> TYPE: DNA
<213> ORGANISM: Homo sapiens

<400> SEQUENCE: 8
ggtgttgtgc tagctgagga gactgtga                                          28

<210> SEQ ID NO 9
<211> LENGTH: 39
<212> TYPE: DNA
<213> ORGANISM: Homo sapiens

<400> SEQUENCE: 9
ggggatatcc accatggatt ttcaggtgca gattttcag                              39

<210> SEQ ID NO 10
<211> LENGTH: 29
<212> TYPE: DNA
<213> ORGANISM: Homo sapiens -continued

<400> SEQUENCE: 10
gcgtctagaa ctggatggtg ggaagatgg                              29

<210> SEQ ID NO 11
<211> LENGTH: 35
<212> TYPE: DNA
<213> ORGANISM: Homo sapiens

<400> SEQUENCE: 11
agcgtcgact tacgtttcag ctccagcttg gtccc                       35

<210> SEQ ID NO 12
<211> LENGTH: 508
<212> TYPE: DNA
<213> ORGANISM: Homo sapiens

<400> SEQUENCE: 12
ccccaagctt gatatcgcca ccatgagatc cagtcctggc aacatggaga ggattgtcat    60
ctgtctgatg gtcatcttct tggggacact ggtccacaaa tcaagctccc aaggtcaaga   120
tcgccacatg attagaatgc gtcaacttat agatattgtt gatcagctga aaaattatgt   180
gaatgacttg gtccctgaat ttctgccagc tccagaagat gtagagacaa actgtgagtg   240
gtcagctttt tcctgctttc agaaggccca actaaagtca gcaaatacag gaaacaatga   300
aaggataatc aatgtatcaa ttaaaaagct gaagaggaaa ccaccttcca caaatgcagg   360
gagaagacag aaacacagac taacatgccc ttcatgtgat tcttatgaga aaaaccacc    420 caaagagttc ctagaaagat tcaaatcact tctccaaaag atgattcatc agcatctgtc   480
ctctagaaca cacggaagtg aagattcc                                      508

<210> SEQ ID NO 13
<211> LENGTH: 419
<212> TYPE: DNA
<213> ORGANISM: Homo sapiens

<400> SEQUENCE: 13
gggggagctc aagatcgcca catgattaga atgcgtcaac ttatagatat tgttgatcag    60
ctgaaaaatt atgtgaatga cttggtccct gaatttctgc cagctccaga agatgtagag   120
acaaactgtg agtggtcagc ttttcctgc tttcagaagg cccaactaaa gtcagcaaat   180
acaggaaaca atgaaaggat aatcaatgta tcaattaaaa agctgaagag gaaaccacct   240
tccacaaatg cagggagaag acagaaacac agactaacat gcccttcatg tgattcttat   300
gagaaaaaac cacccaaaga gttcctagaa agattcaaat cacttctcca aaagatgatt   360
catcagcatc tgtcctctag aacacacgga agtgaagatt ccggttaacg aattcgggg    419

<210> SEQ ID NO 14
<211> LENGTH: 646
<212> TYPE: PRT
<213> ORGANISM: Homo sapiens

<400> SEQUENCE: 14

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

```
Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
             100                 105                 110

Ser Leu Leu Gln Lys Met Ile His Gln His Leu Ser Ser Arg Thr His
             115                 120                 125

Gly Ser Glu Asp Ser Ser Gly Gly Gly Ser Gly Gly Gly Ser
130                 135                 140

Gly Gly Gly Met Ala Gln Val Gln Leu Arg Gln Pro Gly Ala Glu
145                 150                 155                 160

Leu Val Lys Pro Gly Ala Ser Val Lys Met Ser Cys Lys Ala Ser Gly
                 165                 170                 175

Tyr Thr Phe Thr Ser Tyr Asn Met His Trp Val Lys Gln Thr Pro Gly
             180                 185                 190

Gln Gly Leu Glu Trp Ile Gly Ala Ile Tyr Pro Gly Asn Gly Asp Thr
             195                 200                 205

Ser Tyr Asn Gln Lys Phe Lys Gly Lys Ala Thr Leu Thr Ala Asp Lys
210                 215                 220

Ser Ser Ser Thr Ala Tyr Met Gln Leu Ser Ser Leu Thr Ser Glu Asp
225                 230                 235                 240

Ser Ala Val Tyr Tyr Cys Ala Arg Ser His Tyr Gly Ser Asn Tyr Val
                 245                 250                 255

Asp Tyr Phe Asp Tyr Trp Gly Gln Gly Thr Ser Ala Ser Ala Ser Thr
             260                 265                 270

Lys Gly Pro Ser Val Phe Pro Leu Ala Pro Cys Ser Arg Ser Thr Ser
             275                 280                 285

Gly Gly Thr Ala Ala Leu Gly Cys Leu Val Lys Asp Tyr Phe Pro Glu
             290                 295                 300

Pro Val Thr Val Ser Trp Asn Ser Gly Ala Leu Thr Ser Gly Val His
305                 310                 315                 320

Thr Phe Pro Ala Val Leu Gln Ser Ser Gly Leu Tyr Ser Leu Ser Ser
                 325                 330                 335

Val Val Thr Val Pro Ser Ser Ser Leu Gly Thr Gln Thr Tyr Thr Cys
             340                 345                 350

Asn Val Asn His Lys Pro Ser Asn Thr Lys Val Asp Lys Arg Val Glu
             355                 360                 365

Leu Lys Thr Pro Leu Gly Asp Thr Thr His Thr Cys Pro Arg Cys Pro
370                 375                 380

Glu Pro Lys Ser Cys Asp Thr Pro Pro Cys Pro Arg Cys Pro Glu
385                 390                 395                 400

Pro Lys Ser Cys Asp Thr Pro Pro Cys Pro Arg Cys Pro Glu Pro
                 405                 410                 415

Lys Ser Cys Asp Thr Pro Pro Cys Pro Arg Cys Pro Ala Pro Glu
             420                 425                 430

Leu Leu Gly Gly Pro Ser Val Phe Leu Phe Pro Pro Lys Pro Lys Asp
             435                 440                 445

Thr Leu Met Ile Ser Arg Thr Pro Glu Val Thr Cys Val Val Val Asp
450                 455                 460
```

```
Val Ser His Glu Asp Pro Glu Val Gln Phe Lys Trp Tyr Val Asp Gly
465                 470                 475                 480

Val Glu Val His Asn Ala Lys Thr Lys Leu Arg Glu Glu Gln Tyr Asn
                485                 490                 495

Ser Thr Phe Arg Val Val Ser Val Leu Thr Val Leu His Gln Asp Trp
                500                 505                 510

Leu Asn Gly Lys Glu Tyr Lys Cys Lys Val Ser Asn Lys Ala Leu Pro
            515                 520                 525

Ala Pro Ile Glu Lys Thr Ile Ser Lys Ala Lys Gly Gln Pro Arg Glu
        530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Asn Thr
                580                 585                 590

Thr Pro Pro Met Leu Asp Ser Asp Gly Ser Phe Phe Leu Tyr Ser Lys
            595                 600                 605

Leu Thr Val Asp Lys Ser Arg Trp Gln Gln Gly Asn Ile Phe Ser Cys
        610                 615                 620

Ser Val Met His Glu Ala Leu His Asn Arg Tyr Thr Gln Lys Ser Leu
625                 630                 635                 640

Ser Leu Ser Pro Gly Lys
                645
```

COMPOSITIONS, METHODS AND KITS FOR TREATMENT OF CANCER AND AUTOIMMUNE DISEASES

CLAIM OF PRIORITY

This application claims the benefit of U.S. Provisional Application Ser. No. 61/588,486 filed on Jan. 19, 2012, the contents of which are incorporated by reference herein in its entirety.

STATEMENT REGARDING FEDERALLY-SPONSORED RESEARCH AND DEVELOPMENT

Not applicable.

REFERENCE TO SEQUENCE LISTING

The sequence listing submitted electronically on Jan. 18, 2013 having filename "4737_Sequence_Listing_ST25.txt" and its content are herein incorporated by reference in their entirety.

BACKGROUND OF THE INVENTION

1. Field of the Invention

This invention relates generally to the field of compositions and methods for cancer and autoimmune disease research, diagnosis, and treatment. More particularly, this invention relates to fusion proteins, and pharmaceutical compositions, methods and kits comprising the same, for the treatment of cancer and autoimmune diseases.

2. Description of the Related Art

Cytokines are small cell-signaling molecules that are secreted by glial cells and cells of the immune system. They are involved in intercellular communication and stimulate proliferation or differentiation of hematopoietic cells, as well as participate in immune and inflammatory responses of the body.

The innate immune system employs a variety of cells to help protect the body. One example includes natural killer (NK) cells, which are a type of cytotoxic lymphocyte particularly involved in the rejection of tumor cells and other infected or damaged cells. NK cells act by a mechanism of killing utilizing proteins called perforin and granzyme, which cause the targeted cell to die by apoptosis, or programmed cell death. Cytokines play a large role in NK cell activation.

Interleukins are one group of cytokines that are produced by a wide variety of cells and have a significant effect on the function of the immune system. Most interleukins are synthesized by helper $CD4^+$ T lymphocytes and monocytes, macrophages and endothelial cells, and they function to promote the development and differentiation of T, B and hematopoietic cells.

In particular, interleukin-21 (IL-21) is a member of the IL-2 cytokine family and exhibits potent and diverse regulatory effects on NK, T and B cells. Furthermore, IL-21 has been reported to possess potent anti-tumor activity against a variety of cancers not expressing IL-21 receptor (IL-21R) through activation of the immune system, and is currently in clinical trials for renal cell carcinoma and metastatic melanoma. It has previously been observed by one or more of the inventors herein that in addition to its immuno-stimulatory effects, IL-21 exerts direct cytotoxicity on IL-21R expressing diffuse large B cell lymphoma (DLBCL) cell lines and primary tumors both in vitro as well as in xenograft mouse models. Sarosiek et al., Novel IL-21 signaling pathway up-regulates c-Myc and induces apoptosis of diffuse large B-cell lymphomas. *Blood.* 115(3):570-80 (2010). Furthermore, preliminary data by one or more of the inventors herein and others demonstrate that IL-21 may exert similar direct cytotoxicity on mantle cell lymphoma (MCL) cell lines and primary tumors. Gelebart et al., Interleukin-21 effectively induces apoptosis in mantle cell lymphoma through a STAT1-dependent mechanism. *Leukemia.* 23(10): 1836-1846 (2009). However, it has been detected by one or more of the inventors herein that some of the DLBCL and MCL cell lines are partially resistant to IL-21. Therefore, the field of cancer and autoimmune disease treatment and research is in need of a way to augment this effect.

SUMMARY OF THE INVENTION

The present invention provides a method of treating a disorder in a subject, such as cancer or autoimmune disorders in humans, and more specifically, addresses the need for augmentation of the cytotoxic effect of IL-21 in some cancer cells. As such, the present invention is directed to a fusion protein that comprises an IL-21 cytokine as well as an anti-CD20 antibody, and the delivery of this fusion protein to one or more target cells for eliciting a response from the target cell(s). This particular fusion protein was generated based on the finding that an enhanced activity and/or additive cytotoxicity is observed upon combining IL-21 with rituximab, an anti-CD20 antibody, in diffuse large B-cell lymphoma (DLBCL) cell lines. It was therefore hypothesized that an anti-CD20-IL-21 fusion protein (also referred interchangeably herein as a "fusokine"), generated by fusing anti-CD20 monoclonal antibody (mAb) with IL-21 cytokine may exert a better therapeutic effect. Augmented cytotoxicity is possible due to the anti-CD20-IL-21 fusokine's inherent potential to combine direct cytotoxicity of its individual components and to enhance anti-CD20 antibody-dependent cell mediated cytotoxicity (ADCC) by IL-21 mediated stimulation of natural killer (NK) and other effector cells. Furthermore, fusion of IL-21 to the anti-CD20 antibody would also potentially improve IL-21 pharmacokinetics, half-life of the protein, and targeted delivery to CD20 expressing tumors and surrounding immune effector cells.

Accordingly, and in at least one embodiment, the present invention provides a fusion protein comprising at least one IL-21 cytokine and an anti-CD20 antibody. Alternatively, the fusion protein may comprise at least one fragment of either IL-21 cytokine or anti-CD20 antibody, or both. The IL-21 cytokine component(s) of the fusion protein may be fused to either the amino-terminus ("N-terminus") or carboxy-terminus ("C-terminus") of the anti-CD20 antibody component. In at least one embodiment, the fusokine of the present invention may also include a linker peptide between the IL-21 and anti-CD20 components. Furthermore, the fusion protein may include additional components, such as one or more label, chemotherapeutic agent, therapeutic agent, or combinations thereof. The invention also provides pharmaceutical compositions containing the fusion protein packaged with one or more pharmaceutically acceptable excipients, additives, carriers, adjuvants, therapeutic agents, chemotherapeutic agents, or combinations thereof. Kits containing the fusion protein and pharmaceutical compositions described herein are also contemplated. Such kits may include additional reagents and/or instructions for their use.

Additional embodiments of the invention are directed to methods of treating a disorder, such as a cell-proliferative or autoimmune disorder, comprising administering a therapeutically effective amount of an IL-21-anti-CD20 fusion protein or pharmaceutical composition containing such fusion proteins to a subject in need thereof. The fusion proteins and/or pharmaceutical compositions of the present invention may also be utilized in contacting and inhibiting the growth or causing cell death of one or more cells.

Likewise, methods of the invention include antibody-mediated targeted delivery of the fusion proteins and pharmaceutical compositions described herein to one or more cancerous cells or tumors. Such delivery may therefore be useful to target tumor cells or other cells expressing CD20, a protein expressed on the surface of B cells and implicated in at least B cell lymphoma and leukemia. Accordingly, the anti-CD20 antibody component of the fusion protein will recognize CD20 epitopes expressed on certain cancer cells, and will bring the attached IL-21 cytokine upon binding, for cytokine action and immune response stimulation. Another unique aspect of the methods presented herein includes the ability to use a single fusion protein to deliver multiple effector molecules, such as IL-21 cytokines and anti-CD20 antibodies, to one or more target cells in situations where one of the effector molecules may not have elicited a response by the target cell(s) if delivered alone or individually. For example, DLBCL and MCL cell lines are partially resistant to IL-21, however, a synergistic effect is achieved by simultaneous stimulation of both IL-21R and CD20 by the fusion protein of the instant invention, but not by its individual components alone.

The methods, compositions and kits herein described can be used in connection with pharmaceutical, medical, and veterinary applications, as well as fundamental scientific research and methodologies, as would be identifiable by a skilled person upon reading of the present disclosure. These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures in which.

DETAILED DESCRIPTION

Figure 1:
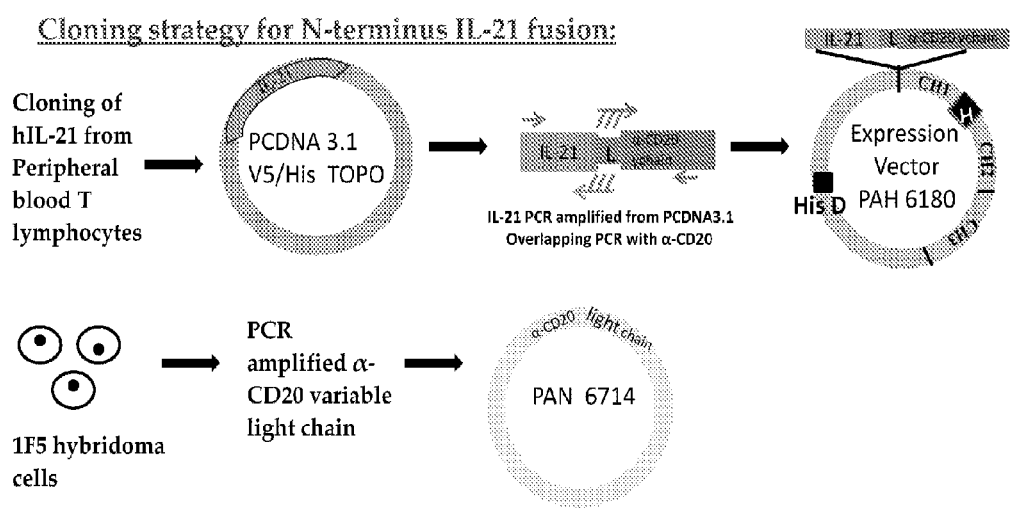
FIG. 1 shows a schematic representation of an embodiment of the present invention comprising the cloning strategy for an anti-CD20-IL-21 fusion protein, wherein the IL-21 component is fused to the amino-terminal end of the CD20 antibody component via a linker peptide (collectively referred herein as "αCD20-N.IL21"). "$C_H1$," "$C_H2$," and "$C_H3$" represent the human $\gamma_3$ heavy chain. "L" represents an $(SGGGG)_3$ (SEQ ID NO:1) linker between the IL-21 component and CD20 antibody component. "H" represents the hinge region of the antibody component.

The present invention is directed to fusion proteins having both IL-21 cytokine and anti-CD20 antibody portions (αCD20-IL21 fusokine), as well as pharmaceutical compositions and kits including the same. The present invention is also directed to methods of using such αCD20-IL21 fusokine in treating cell-proliferative disorders, such as cancer, and autoimmune diseases, as well as methods of targeted cytokine delivery.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Prior to setting forth the invention in detail, it may be helpful to the understanding thereof to define several terms, and these are accordingly set forth below. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

DEFINITIONS

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "subject" refers to an animal. Typically, the terms "subject" and "patient" may be used interchangeably herein in reference to a subject. In at least one embodiment, a "subject" includes a human that is being treated for a disease as a patient.

The term "animal," includes, but is not limited to, mouse, rat, dog, cat, rabbit, pig, monkey, chimpanzee, and human.

In the context of the present invention, the terms "polypeptide" and "protein" are used interchangeably herein. They refer to an amino acid chain or sequence, and include any post-translational modifications thereto (for example phosphorylation or glycosylation). Typically, the term protein is utilized when referring to a full-length product of a gene; however, the use of the term polypeptide would be acceptable.

As used herein, the term "polynucleotide" refers to a nucleic acid chain or sequence of more than one nucleotide. Particularly useful in the present invention are polynucleotides that code for the interleukin-21 (IL-21) gene, or IL-21 fragments, and/or components of anti-CD20 antibodies, or fragments thereof, as well as fusions of the same. The polynucleotides may be included in plasmids, vectors, constructs etc. for expression, cloning, subcloning, transduction, and/or transfection techniques used in the art.

As used herein, the term "gene" refers to a polynucleotide derived from a chromosome that codes for RNA and/or protein. A gene, as used herein, may or may not include all introns, exons, promoter regions, enhancer regions, non-coding regions, and the like, that are associated with the specific gene. A gene may, but not necessarily, code for a functional protein. Additionally, in some embodiments, a fragment of a gene may be used in the methods herein.

All genes and gene products (including RNA and protein), and their respective names disclosed herein are intended to encompass any corresponding homologs from any species for which the compositions and methods disclosed herein are applicable. When a gene or gene product from a particular species is disclosed, it is understood that this disclosure is intended to be exemplary only and is not to be interpreted as a limitation unless the context in which it appears clearly indicates otherwise. For example, the genes and gene products disclosed herein, which in some embodiments relate to mammalian (including human) nucleic acid and/or amino acid sequences, are intended to encompass homologous, orthologous, and/or paralogous genes and gene products from other animals including, but not limited to, other mammals, fish, reptiles, amphibians, birds, and other vertebrates.

As used herein, the term "promoter" refers to a regulatory region of a gene that provides a recognition site for the transcriptional machinery of a cell, to facilitate transcription of the gene. A gene can have more than one promoter, and most promoters are upstream of the transcription initiation site, although downstream positioning of the promoter is contemplated. "Upstream" refers to a location closer to the 5' end of the nucleic acid sequence than the reference point. "Downstream" refers to a location closer to the 3' end of the nucleic acid sequence as compared to the reference point. Furthermore, a promoter may be utilized in the present invention to regulate transcription of gene fragments and/or fusions of genes or gene fragments.

The terms "amino-terminal" and "carboxy-terminal" are used interchangeably with the terms "N-terminal" and "C-terminal," respectively. The terms are used in reference to a portion of a polypeptide, such as a portion of an antibody, to describe the relative position as is commonly understood in the art. For example, if a cytokine is fused to the N-terminal end of an antibody it is either located proximal to or connected directly to the amino terminus of the antibody.

As used herein, a "cell-proliferative disorder" refers to any disorder that is characterized by abnormal proliferation of cells. In some embodiments, the cell-proliferative disorder is cancer or a cancerous tumor, and may be of any organ or tissue, and may be malignant or benign. In other embodiments, the cell-proliferative disorder is a benign growth or non-cancerous tumor.

The term "cancer" or "cancerous," as used herein, refers to the uncontrolled growth and division of cells, resulting in an overgrowth of cells or mass or growth (i.e., tumor). It also encompasses the ability of the cells to metastasize, or migrate from the original site to distant sites in the subject's body. When referring to a "tumor," a cancerous tumor is often referred to as a "malignant tumor"; however, reference to a "tumor" alone may also refer to a malignant tumor in some contexts. "Cancer" collectively refers to individual cancerous cells and malignant tumors, such as more than one, or a mass, of cancerous cells. Additionally, references to "cancer" include primary tumors that grow at the site of tumor origination and proceeded to form a cancerous growth, as well as and metastatic lesions or one or more tumors that are derived from a malignant cell(s) of the primary tumor but grow at a site remote from the primary tumor. However, the use of the term "cancer" does not necessarily mean that a primary tumor has yet metastasized. Some cancers may be either indolent or aggressive initially. In contrast, some cancers may begin as an indolent lesion and change over time to become aggressive. As such, a primary tumor may remain indolent for a period of time and grow very slowly with no metastatic occurrence and eventually become aggressive and grow rapidly and metastasize. Use of the terms "cancer" and "tumor" would encompass all such possibilities described above as utilized in the present invention.

As would be understood by those of skill in the art, the methods, compositions and kits of the present invention are contemplated to be applicable to cancer(s). Such cancers include, but are not limited to, cancers originating from lymphatic cells, particularly B-cells. The types of cancer that may originate in the aforementioned cells include lymphoid leukemia and lymphoma.

As used herein, an "autoimmune disorder" refers to any of a group of diseases characterized by abnormal functioning of the immune system causing one's immune system to produce antibodies against its own tissue(s). Non-limiting examples of autoimmune disorders contemplated to be applicable to the present invention include lupus, rheumatoid arthritis, and Grave's Disease.

As used herein, "treatment" or "treating" refers to arresting or inhibiting, or attempting to arrest or inhibit, the development or progression of a disease and/or causing, or attempting to cause, the reduction, suppression, regression, or remission of a disease and/or a symptom thereof. As would be understood by those skilled in the art, various clinical and scientific methodologies and assays may be used to assess the development or progression of a disease, and similarly, various clinical and scientific methodologies and assays may be used to assess the reduction, regression, or remission of a disease or its symptoms. "Treatment" refers to both therapeutic treatment and prophylactic or preventative measures. Those in need of treatment include those who already have the disease, as well as those with a propensity or predisposition for the disease and those in whom the disease is to be prevented. In at least one embodiment, the disease being treated is cancer, such as described above. In other embodiments, the disease being treated is an autoimmune disease as previously described.

As used herein, a "cytokine" refers to a secreted protein, or active fragment thereof, having a role in cell signaling that modulates the activity of cells. Cytokines typically stimulate proliferation and/or differentiation of cells. They also participate in immune and inflammatory responses within the body. Examples of cytokines include the interleukins, interferons, tumor necrosis factors, chemokines, colony-stimulating factors for immune cell precursors, and the like. Particularly useful in the present invention is interleukin-21 and fragments thereof.

As used herein, "interleukin-21" or "IL-21" refers to any mammalian IL-21, such as human IL-21, mouse IL-21, or an active species or allelic variant, fragment or derivative thereof. IL-21 has been shown to modulate natural killer (NK) cells and cytotoxic T cells, as well as bind and provide a cytotoxic effect on some lymphoma cells, thus having an effect on the immune response.

As used herein, the term "fragment" refers to a portion of a compound or molecule, such as fragments of a polynucleotide or polypeptide. For example, when referring to a polypeptide, a fragment is a plurality of amino acids comprising less than the entire length of the polypeptide or protein. When referring to a polynucleotide, a fragment is a plurality of nucleotides comprising less than the entire length of the polynucleotide. A fragment may also include a polymerase chain reaction (PCR) product or fragment resulting from enzymatic cleavage. A fragment of a compound can share up to 99%, 95%, 90%, 85%, 80%, 75%, 70%, 65%, or 60% of its sequence with the parent or full-length compound. A "functional fragment" is defined as a polynucleotide or polypeptide of shorter length than the corresponding full-length gene, RNA or protein that retains the activity and functionality of the corresponding full-length version. For example, a functional fragment may correspond to an epitope, binding site, recognition site, or other minimally required sequence for activity.

The terms "effective amount" and "therapeutically effective amount" are used interchangeably herein, and as applied to the fusion proteins and pharmaceutical compositions described herein mean the quantity necessary to render the desired therapeutic result. For example, an effective amount is a level effective to treat, cure, or alleviate the symptoms of a disorder for which the fusion protein, or composition thereof, is being administered. Amounts effective for the particular therapeutic goal sought will depend upon a variety of factors including, but not limited to, the particular disorder being treated and its severity and/or stage of development/progression; the bioavailability and activity of the specific fusion protein or pharmaceutical composition used; the route or method of administration and introduction site on the subject; the rate of clearance, bioabsorption or metabolism of the specific protein or composition and other pharmacokinetic properties; the duration of treatment; inoculation regimen and frequency; drugs used in combination or coincident with the specific protein or composition; the age, body weight, sex, diet, physiology and general health of the subject being treated; and like factors well known to one of skill in the relevant scientific art. Some variation in dosage will necessarily occur depending upon the condition of each subject being treated, and the physician or other individual administering treatment will, in any event, determine the appropriate dosage for an individual patient.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

As used herein, "disease" refers to a disorder, disease or condition, or other departure from healthy or normal biological activity which impairs normal function. The terms "disease", "disorder", and "condition" may be used interchangeably throughout the present specification. The condition may be caused by sporadic or heritable genetic abnormalities. The condition may also be caused by non-genetic abnormalities. The disease may be present in a subject with clinical or sub-clinical symptoms; however, the subject may also be asymptomatic at the time of diagnosis. The disease may include a benign growth or benign tumor (i.e., non-cancerous growth), as well as cancer (i.e., cancerous cell or cancerous tumor). Additionally, diseases applicable to the present invention include autoimmune disorders.

As used herein, "peptide linker" means one or more peptides or series of amino acids disposed between and/or coupling two proteins, or fragments thereof (e.g., an antibody and a cytokine). The peptide linker may be comprised of any combination or series of amino acids. In at least one embodiment, the peptide linker is a mixed series of predominantly glycine and serine residues and is about 10-15 amino acids in length. Particularly useful in the present invention is a peptide linker with a sequence comprising $(SGGGG)_3$ (SEQ ID NO: 1).

The terms "antibody" and "immunoglobulin" may be used interchangeably, and are defined herein as a protein synthesized by an animal or a cell of the immune system in response to an antigen or immunogen. The term antibody as used herein also refers to fragments and/or functional derivatives thereof. Antibodies are characterized by specific affinity to a site on the antigen referred to as an "antigenic determinant" or an "epitope". Antigens may be naturally occurring or artificially engineered variants or derivatives. Artificially designed or engineered variants of naturally occurring antibodies, as well as fusion proteins wherein a component of the fusion protein is an antibody, and artificially designed or engineered antibodies not occurring in nature are all included in the current definition. Such variants or derivatives include conservatively substituted amino acids and other forms of substitution. Furthermore, the present invention encompasses antibodies, or fragments thereof, that have been chemically or genetically modified in amino acid sequence(s) by addition and/or deletion of amino acids. The antibodies of the invention may also be chemically modified in one or more of their functional chemical groups by deletions, additions, rearrangement, oxidation, reduction, etc. while maintaining antigen binding affinity. The immunoglobulin molecules utilized in the present invention can be of any type (e.g., IgG, IgE, IgM, IgD, IgA and IgY), class (e.g., IgA1, IgA2, IgG1, IgG2, IgG3, and IgG4) or subclass of immunoglobulin molecule.

As used herein, reference to antibodies may be designated interchangeably by an "a" or "anti-" or "α" preceding the antigenic target name. For example, aCD20, anti-CD20, and αCD20 all refer to antibodies raised against and/or recognizing a CD20 antigen.

As used herein, a "label" refers to a composition detectable by biochemical, immunochemical, chemical, spectroscopic, radiographic, or photochemical means. Labels may include radionuclides, such as but not limited to $^{32}P$, $^{35}S$ and $^{51}Cr$; fluorescent dyes; enzymes; reagents; biotin-streptavidin; dioxigenin; haptens and proteins for which antibodies or antisera are available; nucleic acid molecules with complementary sequences to a particular target; heterologous polypeptides; drugs; or toxins.

Fusion Protein

As noted previously, the present invention is directed to a protein comprising a fusion of a cytokine with an antibody. More specifically, in at least one embodiment, the fusion protein, or fusokine, includes an anti-CD20 antibody linked to a IL-21 cytokine.

Interleukin-21 (IL-21) is a protein encoded by the approximately 8.43 kb human IL21 gene on chromosome 4. As discussed previously herein, IL-21 is a cytokine that has regulatory effects on cells of the immune system and also possesses potent anti-tumor activity.

B-lymphocyte antigen CD20 (CD20) is a phosphoprotein expressed on the surface of B-cells, and has been implicated in B cell lymphomas and leukemia. It is encoded by the MS4A1 gene in humans on chromosome 11. CD20 is a common target of monoclonal antibodies, such as rituximab, ibritumomab tiuxetan, and tositumomab, for the treatment of B cell lymphomas and leukemias.

In at least one embodiment, the present invention provides a fusion protein comprising at least one IL-21 cytokine and an anti-CD20 antibody. Furthermore, embodiments of the fusion protein may comprise functional fragments of either IL-21 cytokine(s), anti-CD20 antibody, or both. It would be understood by those skilled in the art that each embodiment described herein could utilize a functional fragment of either IL-21 or anti-CD20 antibody in place of each of their full-length counterparts. Preferably, the fragments utilized would maintain the full-length counterpart functionality. However, it is contemplated that partially functional equivalents of each may be utilized.

The IL-21 cytokine component(s) may be fused to either the N-terminus or C-terminus of the anti-CD20 antibody. Additionally, the cytokine-antibody fusion may include a linker peptide between the cytokine and antibody components (see FIG. 1). In at least one embodiment, the linker peptide comprises the sequence $(SGGGG)_3$ (SEQ ID NO:1), however, other embodiments of the invention may utilize other linker peptides, such as those commonly used in the art, as previously described herein and understood to provide similar functionality. In some embodiments, no linker peptide is necessary to provide a functional fusion protein, for instance when the cytokine is fused to the C-terminus of the antibody (see FIG. 2).

Furthermore, antibody-cytokine fusions of the present invention may be further recombinantly fused or conjugated to effector molecules and/or molecular labels for detection. Each of the components of the fusokine will now be discussed in greater detail.

a. Cytokine Component

The cytokines utilized in the present invention are inclusive of those from all classes and species. Most preferably, however, the cytokines are human or humanized cytokines and fragments thereof.

Cytokines utilized in the present invention, such as IL-21, may also be described or specified in terms of their ability to bind analogous, orthologous, or homologous cytokine receptors. Cytokines that do not bind any other analog, ortholog, or homolog of the interleukin-21 receptor (IL-21R) are also included. Cytokines that bind IL-21R, or a fragment thereof, with at least 95%, at least 90%, at least 85%, at least 80%, at least 75%, at least 70%, at least 65%, at least 60%, at least 55%, and at least 50% identity (as calculated using methods known in the art) to IL-21R, or a fragment thereof, are also included in the present invention. In specific embodiments, cytokines of the present invention bind with murine, rat and/or rabbit homologs of human IL-21R, or a fragment thereof retaining IL-21R binding activity.

Cytokines that do not bind IL-21R, or a fragment thereof, with less than 95%, less than 90%, less than 85%, less than 80%, less than 75%, less than 70%, less than 65%, less than 60%, less than 55%, and less than 50% identity (as calculated using methods known in the art) to IL-21R, or a fragment thereof, are also included in the present invention. Cytokines utilized in the present invention may also be described or specified in terms of their binding affinity to their receptor, such as IL-21R, or a fragment thereof. Binding affinities include those with a dissociation constant ($K_d$) ranging from about 0.05 μM to about 0.25 μM. In at least one embodiment, the dissociation constant is about 0.16 μM.

The cytokines utilized in the invention include derivatives that are modified, such as by the covalent attachment of any type of molecule to the cytokine which does not prevent the cytokine from recognizing its target receptor and/or modulating a response by its target cell. Non-limiting examples of the cytokine derivatives include cytokines that have been modified by glycosylation, acetylation, pegylation, phosphorylation, proteolytic cleavage, amidation, and linkage to a cellular ligand or other protein. Any of numerous chemical modifications may be carried out by known techniques, including, but not limited to, specific chemical cleavage, acetylation, formylation, or metabolic synthesis.

b. Antibody Component

The antibodies utilized in the present invention are inclusive of all species, and the antigenic target, e.g., CD20, can be from any species. Most preferably, the antibodies are human antigen-binding antibodies, and fragments thereof, and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the hinge region, $C_H1$, $C_H2$, and/or $C_H3$ domains. Single chain antibodies are formed by linking the heavy and light chain fragments of the $F_v$ region via an amino acid bridge, resulting in a single chain polypeptide. Also included in the invention are antigen-binding fragments comprising any combination of variable region(s) with a hinge region, $C_H1$, $C_H2$, and/or $C_H3$ domains.

The antibodies utilized in the present invention may also be monospecific, bispecific, trispecific, or multispecific. Multispecific antibodies may be specific for different epitopes of a polypeptide or may be specific for both a polypeptide and its heterologous epitope, such as a heterologous polypeptide, for example, an antibody specific for CD20 proteins from both mouse and human.

Antibodies utilized in the present invention may also be described or specified in terms of their cross-reactivity. Antibodies that do not bind any other analog, ortholog, or homolog of CD20 are included. Antibodies that bind CD20, or a fragment thereof, with at least 95%, at least 90%, at least 85%, at least 80%, at least 75%, at least 70%, at least 65%, at least 60%, at least 55%, and at least 50% identity (as calculated using methods known in the art) to CD20, or a fragment thereof, are also included in the present invention. In specific embodiments, antibodies of the present invention cross-react with murine, rat and/or rabbit homologs of human CD20, or a fragment thereof, and with the corresponding epitopes thereof. Antibodies that do not bind CD20, or a fragment thereof, with less than 95%, less than 90%, less than 85%, less than 80%, less than 75%, less than 70%, less than 65%, less than 60%, less than 55%, and less than 50% identity (as calculated using methods known in the art) to CD20, or a fragment thereof, are also included in the present invention.

The present invention also contemplates the use of antibodies that bind CD20, or a fragment thereof, encoded by polynucleotides which hybridize to a CD20 polynucleotide under stringent hybridization conditions. "Stringent hybridization conditions" in the context of nucleic acid hybridization experiments, such as Southern and Northern hybridizations, are sequence-dependent, and are different under various environmental parameters. Longer sequences hybridize specifically at higher temperatures. Generally, highly stringent hybridization and wash conditions are selected to be about 5 degrees Celsius lower than the thermal melting point ($T_m$) for the specific sequence at a defined ionic strength and pH. Typically, under "stringent conditions" a probe will hybridize to its target subsequence, but to no other sequences.

Antibodies utilized in the present invention may also be described or specified in terms of their binding affinity to CD20, or a fragment thereof. Preferred binding affinities include those with a dissociation constant ($K_d$) from about $5 \times 10^{-9}$ M to about $10^{-9}$ M.

The antibodies utilized in the invention include derivatives that are modified, such as by the covalent attachment of any type of molecule to the antibody which does not prevent target epitope(s) recognition and/or binding, and further modulating a response by the target cell. Non-limiting examples of the antibody derivatives include antibodies that have been modified, such as by glycosylation, acetylation, pegylation, phosphorylation, proteolytic cleavage, amidation, and linkage to a cellular ligand or other protein. Any of numerous chemical modifications may be carried out by known techniques, including, but not limited to specific chemical cleavage, acetylation, formylation, or metabolic synthesis. In a particularly useful embodiment, the antibody is linked to at least one other protein.

For instance, the anti-CD20 antibody is linked to at least one IL-21 cytokine, thus providing the fusion protein, or fusokine, of the present invention.

Methods of Producing the Fusion Protein

The antibodies, and fusion proteins comprising such antibodies, useful in the present invention may be generated by any suitable method known in the art. Monoclonal antibodies, and fusion proteins comprising such antibodies, can be prepared using any of the techniques known in the art, including the use of hybridoma, recombinant, and phage display technologies, or a combination thereof. The term "monoclonal antibody" or "mAb" as used herein is not limited to antibodies produced through hybridoma technology. The term refers to any antibody, and fusion proteins comprising such an antibody, that is derived from a single clone, including any eukaryotic, prokaryotic, or phage clone, and not the method by which it is produced. Methods for producing and screening for specific antibodies using hybridoma technology are routine and well known in the art and are briefly discussed in the Examples with regard to antibody-interleukin fusions. Furthermore, vectors encoding the fusion proteins of the invention can be stabled expressed in sp2/0 hybridoma and CHO cells expressing the desired antibody κ light chain, such as the anti-CD20 κ light chain. Accordingly, the present invention provides methods of generating monoclonal antibody-cytokine fusions comprising culturing a hybridoma cell secreting an antibody-cytokine fusion of the invention, as well as using CHO cells to express the fusions. The monoclonal antibody-cytokine fusions produced by the methods described are also provided by the present invention.

Antibody fragments useful in the present invention that recognize specific epitopes may be generated by known techniques. For example, Fab and F(ab')2 fragments may be generated by proteolytic cleavage of immunoglobulin molecules, using enzymes such as papain (to obtain Fab fragments) or pepsin (to obtain F(ab')2 fragments), which contain the variable region, the light chain constant region and the $C_H1$ domain of the heavy chain).

In some instances, it may be desirable to use chimeric, humanized, or human antibodies in the antibody-cytokine fusions of the invention. A chimeric antibody is a molecule in which different portions of the antibody are derived from different animal species, such as a variable region derived from a murine monoclonal antibody and a human immunoglobulin constant region. Methods for producing chimeric antibodies are known in the art and may include splicing genes from a mouse antibody molecule of appropriate antigen specificity together with genes from a human antibody molecule of appropriate biological activity. Humanized antibodies are antibody molecules from a non-human species antibody that binds the desired antigen having one or more complementarily determining regions (CDRs) from the non-human species and a framework region from a human immunoglobulin molecule. Completely human antibodies may be desirable for therapeutic treatment of human patients. Human antibodies can be made by a variety of methods known in the art.

Anti-CD20 antibodies, or antibody fragments thereof, useful in the present invention may bind to one or more epitopes comprising amino acid sequences such as, but not limited to, IPAGIYPI (SEQ ID NO:2) and HFLKMESLN-FIRAHTP (SEQ ID NO:3), which are present in the small and large loop of CD20, respectively. Useful anti-CD20 antibodies, or antibody fragments thereof, may also specifically bind to one or more epitopes on a 297 amino acid CD20 polypeptide having the amino acid sequence, or a portion thereof, shown below in SEQ ID NO:4.

```
                                            (SEQ ID NO: 4)
MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL

LAATEKNSRKCLVKGKMIMNSLSLFAAISGMILSIMDILNIKISHFLKME

SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSP
```

Highlighted residues indicate epitopes of CD20 as shown in SEQ ID NO:2 and SEQ ID NO:3.

The antibody-cytokine fusions of the present invention can be produced by any method known in the art for production of proteins and antibodies, in particular, by chemical synthesis or recombinant expression techniques.

Recombinant expression of an antibody-cytokine fusion of the invention, or fragment, derivative or analog thereof, requires construction of cloning and/or expression vectors containing polynucleotides that encode the antibody, or antibody fragment, and the at least one cytokine, or cytokine fragment. Once polynucleotides encoding an antibody molecule or a heavy or light chain of an antibody, or portion thereof (such as the heavy or light chain variable domain), and the cytokine(s) are obtained, the vectors for the production of the antibody-cytokine fusion proteins may be produced by recombinant DNA technology using techniques well known in the art. Accordingly, upon transcription into RNA and translation into protein, the resulting protein will include both an antibody portion (such as αCD20) and a cytokine portion (such as IL-21). Methods well known to those skilled in the art can be used to construct cloning and/or expression vectors containing antibody and cytokine coding sequences and appropriate transcriptional and translational control signals. These methods include, for example, in vitro recombinant DNA techniques, synthetic techniques, and in vivo genetic recombination. The invention, thus, provides replicable vectors comprising nucleotide sequences encoding an antibody molecule, or a heavy or light chain thereof, or a heavy or light chain variable domain, and a cytokine molecule, or a fragment thereof, operably linked to a promoter. These vectors may include the nucleotide sequence encoding the constant region of the antibody molecule and the variable domain of the antibody may be cloned into the vector for expression of the entire heavy or light chain. The vectors may further include linker sequences inserted between the antibody component and the cytokine component(s). Furthermore, the antibody component and the cytokine component may be cloned into the expression vector such that the resultant antibody-cytokine fusion is at least one cytokine fusion to the N- or C-terminus of the antibody molecule.

The resulting expression vectors are transferred to host cells by conventional techniques known in the scientific art, including but not limited to transduction and transfection. Transduced or transfected cells are then cultured by known techniques to produce an antibody-cytokine fusion of the invention. Therefore, the invention also includes cultured host cells containing a polynucleotide encoding an antibody-cytokine fusion of the invention. For long-term, high-yield production of recombinant fusion proteins, stable expression may be preferred. For example, cell lines which stably express the antibody-cytokine fusion molecule may be engineered.

Following production of an antibody-cytokine fusion molecule of the invention, it may be purified by any method known in the art for purification of an immunoglobulin molecule, for example, by chromatography, centrifugation, differential solubility, or by any other technique known in the art for the purification of proteins.

Pharmaceutical Compositions & Kits

The present invention also provides pharmaceutical compositions comprising the IL-21-anti-CD20 fusion protein in combination with one or more pharmaceutically acceptable carriers described herein.

The term "carrier" refers to a diluent, adjuvant, excipient, and/or vehicle with which the fusion protein is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition may also contain wetting or emulsifying agents or suspending/diluting agents, or pH buffering agents, or agents for modifying or maintaining the rate of release of the fusion protein. These compositions can take the form of solutions, suspensions, emulsion, tablets, pills, capsules, powders, sustained-release formulations and the like. Formulations can include standard carriers such as pharmaceutical grades of mannitol, lactose, sodium saccharine, starch, magnesium stearate, cellulose, magnesium carbonate, etc. Such compositions will contain a therapeutically effective amount of the fusion protein together with a suitable amount of carrier so as to provide the proper form to the patient based on the mode of administration to be used.

For intravenous administration, the compositions may be packaged in solutions of sterile isotonic aqueous buffer. Where necessary, the composition may also include a solubilizing agent. The components of the composition are supplied either separately or mixed together in unit dosage form, for example, as a dry lyophilized powder or concentrated solution in a hermetically sealed container such as an ampoule or sachette indicating the amount of active agent. If the composition is to be administered by infusion, it can be dispensed with an infusion bottle containing sterile pharmaceutical grade water or saline. Where the composition is administered by injection, an ampoule of sterile water, saline, or other appropriate solvent may also be provided so that the ingredients may be mixed prior to injection.

Moreover, if a packaging material is utilized to package the pharmaceutical composition, it may be biologically inert or lack bioactivity, such as plastic polymers, silicone, etc. and may be processed internally by the subject without affecting the effectiveness of the fusion protein packaged and/or delivered therewith.

Additionally, the fusion proteins and/or pharmaceutical compositions may be packaged with additional agents. The additional agents may be conjugated to the fusion proteins or packaged within a pharmaceutical composition comprising the fusion protein. The agents include, but are not limited to, chemotherapeutic agents (i.e., cytotoxins), radioactive isotopes, and other therapeutic agents. A chemotherapeutic agent or cytotoxin includes any agent that is detrimental to cells (i.e., kills cells through apoptotic pathways or necrotic pathways, causes growth arrest of cells, or combinations of these events). Examples include, but are not limited to, paclitaxol, lidocaine, cytochalasin B, ethidium bromide, emetine, mitomycin, actinomycin D, etoposide, tenoposide, vincristine, vinblastine, colchicin, doxorubicin, gramicidin D, daunorubicin, dihydroxy anthracin dione, mitoxantrone, mithramycin, 1-dehydrotestosterone, glucocorticoids, procaine, tetracaine, propranolol, and puromycin and analogs or homologs thereof. Examples of therapeutic agents include, but are not limited to, alkylating agents (e.g., mechlorethamine, thioepa chlorambucil, melphalan, carmustine and lomustine, cyclothosphamide, dibromomannitol, busulfan, streptozotocin, mitomycin C, and cis-dichlorodiamine platinum (cisplatin)), antimetabolites (e.g., methotrexate, 6-thioguanine, 6-mercaptopurine, cytarabine, 5-fluorouracil decarbazine), anthracyclines (e.g., daunorubicin and doxorubicin), antibiotics (e.g., dactinomycin and actinomycin), mithramycin, bleomycin, and anthramycin (AMC)), and anti-mitotic agents (e.g., vincristine, vinblastine and monomethyl auristatin E (MMAE)).

The therapeutic agents utilized may also be used for modifying a given biological response, thus the therapeutic agent is not to be limited to classical chemical therapeutic agents. For example, the therapeutic agent may be a protein or fragment thereof possessing a desired biological activity. For example, such proteins may include a toxin such as ricin A or diphtheria toxin; other cellular factors such as tumor necrosis factor, interferons, interleukins, lymphokines, granulocyte colony stimulating factor, granulocyte macrophage colony stimulating factor, platelet derived growth factor, tissue plasminogen activator; an apoptotic agent (e.g., TNF-alpha, TNF-beta, or Fas Ligand); a thrombotic agent; or an anti-angiogenic agent (e.g., angiostatin or endostatin).

The present invention also provides kits comprising a fusion protein as described herein. The kits may further be used in the methods described herein. The kits may also include at least one reagent and/or instructions for their use. Also, the kit may include one or more containers filled with reagent(s) and/or one or more components of the pharmaceutical compositions of the invention. One or more container of the kits provided may also comprise a fusion protein of the invention, preferably in a purified form. The kits may also comprise a control composition, such as a control antibody that may include antibodies that bind CD20 as well as antibodies that do not bind, and/or a control interleukin, which may include interleukins that bind the IL-21 receptor (IL-21R), as well as those that do not bind.

In certain embodiments, the kits may additionally include reagents and means for detecting the binding of the fusion protein to epitopes and/or receptor proteins of interest (e.g., CD20 and/or IL-21R). The means of allowing detection may be by conjugation of detectable labels or substrates, such as fluorescent compounds, enzymes, radioisotopes, heavy atoms, reporter genes, luminescent compounds, or additional antibodies against the anti-CD20 antibody component and/or IL-21 component. As it would be understood by those skilled in the art, additional detection or labeling methodologies may be used in the kits provided.

In some embodiments, the kits include a cloning or expression vector encoding for the αCD20-IL21 fusokine, or cells transfected or otherwise imbued with such vector and capable of expressing the αCD20-IL21 fusokine therefrom.

Methods of Using the IL-21-Anti-CD20 Fusion Protein

The present invention is further directed to methods of using the αCD20-IL21 fusokine, such as for the treatment and/or inhibition of a disorder. Such methods and/or uses involve administering a therapeutically effective amount of the fusion proteins or pharmaceutical compositions of the invention to a subject, preferably a mammal, and most preferably a human, for treating one or more of the disorders described previously herein, such as but not limited to cancers, lymphomas, leukemias, and autoimmune disorders.

Administration may be locally confined to a single cell or tissue and/or systemically in the subject. It may be desirable to administer the fusion proteins and pharmaceutical compounds of the invention locally to the area in need of treatment, such as areas including one or more tumor. This method of administration may be achieved by, for example, and not by way of limitation, local infusion during surgery, topical application such as in conjunction with a wound dressing after surgery, injection, catheter, or via an implant or porous membrane. When administering a protein, particularly a fusion protein of the invention, care must be taken to use materials which do not absorb the protein, as this would frustrate or delay effective release, if so desired.

In some embodiments, the fusion protein or pharmaceutical composition containing the same can be delivered in a controlled release system. Such methods may include the use of a pump for administration, such as use of an intravenous drip. In another embodiment, a controlled release system can be placed in the proximity of the therapeutic target, such as a tumor, requiring only a fraction of the dose required if dosed systemically.

The fusion proteins and compositions of the invention can be used to treat, alleviate, inhibit or prevent disorders associated with expression and/or activity of a cytokine receptor (e.g., IL-21R) and/or other cell-surface molecule (e.g., CD20). In preferred embodiments, the disorder being treated includes a cell-proliferative disorder or an autoimmune disease. The cell-proliferative disorder may be cancer, such as lymphoma. The methods provided are particularly useful in treatment of B-cell lymphomas.

Based on the dual nature of the fusion protein, by virtue of having both IL-21 activity and anti-CD20 properties, it is possible to deliver multiple therapeutic molecules and effectively elicit both IL-21 and anti-CD20 responses in one or more cells, or one or more cells and surrounding immune effector cells, such as NK cells, macrophages and/or neutrophils. For example, the anti-CD20 component of the fusion protein may target the protein to CD20 expressing cells while the IL-21 component(s) induce a response by surrounding immune effector cells, providing antibody dependent cellular cytotoxicity (ADCC) activity. Such immune effector cells may express the receptor for IL-21, referred to as "IL-21R", on their cell surface and provide a mechanism for IL-21 activation of the cells. The activation of the immune effector cells by the IL-21 component(s) of the fusion protein further provides a mechanism for the killing of the anti-CD20 targeted cell, thus providing an enhanced cellular response or anti-tumor activity. Additionally, when the cell expresses the IL-21R itself, the IL-21 component(s) of the fusion protein may directly bind one or more receptors and initiate an anti-tumor response. Thus, a method of targeting multiple receptors on a cell with a single fusion protein is provided by the methods, kits and compositions provided by the present invention.

The fusion proteins of the invention may also be utilized in pharmaceutically acceptable compositions in the methods provided herein.

As would be understood by those skilled in the art, the disorders being treated would not necessarily need to have aberrant expression or activity of a cytokine receptor and/or other cell-surface molecule. The cytokine receptor and/or other cell-surface molecule may be of normal expression and/or activity, yet provide a means for modulation of the desired therapeutic response in the cell, surrounding cells and/or body of the subject being treated.

Furthermore, it would be understood by those skilled in the art that the therapeutic methods described would not only apply to treatment in a subject, but could be applied to cell cultures, organs, tissues, or individual cells in vivo, ex vivo or in vitro. Also, due to the fusion proteins of the invention comprising an anti-CD20 antibody component, it is possible to provide targeted delivery of the fusion proteins to cancer cells and tumors that may express CD20 on the cell surface. Such delivery may inhibit growth of the cell(s), kill the cell(s), and/or cause an immunological response targeted at the CD20 expressing cancer cells and tumors. Additionally, a method of enhancing antibody dependent cellular cytotoxicity activity (ADCC) against cells expressing CD20 in a subject by administration of the fusion protein is provided by the present invention due to the fusion protein's ability to mediate stimulation of NK and other effector cells through its IL-21 component(s).

It would also be understood by a skilled artisan how to use the fusion proteins of the present invention for diagnostic or therapeutic purposes without undue experimentation based on the teachings provided throughout the specification.

The fusion proteins of the invention may also be utilized in combination with other fusion proteins (e.g., other cytokine-antibody fusions), antibodies, or cytokines during treatment. Such combination treatments may further enhance the therapeutic effects of treatment with the fusion proteins of the invention. The fusion proteins may also be administered alone or in combination with other types of therapeutically effective treatments, such as but not limited to radiation therapy, surgery, biologics therapy, transplants, hyperthermia, hypothermia, laser therapy, photodynamic therapy, gene therapy, chemotherapy or anti-cancer agents, hormonal therapy, immunotherapy, and combinations thereof). The agents useful in the treatments are previously described herein.

The other treatments may also be carried out by linking the treatment modality (e.g., anti-cancer agent or gene therapy vector) to the fusion protein (i.e., fusion of the components), when applicable.

The amount of the fusion protein or pharmaceutical compound of the invention which will be effective in the treatment, inhibition and/or prevention of a disease or disorder can be determined by standard clinical techniques. Additionally, in vitro assays may be employed to help identify optimal dosage ranges. The precise dose to be utilized will also depend on the route of administration, and the seriousness of the disorder, and should also be decided according to the sound medical judgment of the clinician and each patient's individual circumstances. The specific therapeutically effective dose level for any particular patient will depend upon a variety of factors including: the type and degree of the response to be achieved; the specific composition and other agent(s), if any, employed; the age, weight, general health, sex and diet of the patient; the time of administration, route of administration, and rate of excretion of the composition; the duration of the treatment; other drugs (such as a chemotherapeutic agents) used in combination or coincidental with the composition; and any other factors well known in the medical arts. Effective dosages may also be extrapolated from dose-response curves derived from in vitro or animal model testing systems.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

In order to facilitate understanding of the following examples, certain frequently occurring methods and/or terms will be described.

"Plasmids" are designated by a lower case "p" preceded and/or followed by capital letters and/or numbers. The starting plasmids used herein are either commercially available, publicly available, or can be constructed from available plasmids in accord with published procedures. In addition, equivalent plasmids to those described are known in the art and may be substituted where appropriate and will be apparent to the ordinarily skilled artisan.

"Primers" refer to single stranded polydeoxynucleotide strands, which may be chemically synthesized. Such primers are utilized in polymerase chain reactions (PCR) to synthesize a fragment of DNA to be used in the cloning methods described in more detail below.

"Ligation" or "ligate" refers to the process of forming phosphodiester bonds between two double stranded nucleic acid fragments. Ligation may be accomplished using known buffers and conditions with an appropriate ligase enzyme, such as T4 DNA ligase.

"Clone" or "cloning" refers to a set of experimental methods that are used to assemble recombinant DNA molecules and replicate them in a host organism, such as bacteria. The final DNA product of a cloning process may be used for expression of the corresponding protein product in cells.

Example 1

Design and Construction of αCD20-IL-21 Fusokine

The heavy and light chain variable regions of αhuCD20 were isolated by polymerase chain reaction (PCR) from the 1F5 hybridoma cell line (ATCC) using the following PCR primers:

```
Heavy Chain
1st PCR Primers
Forward
                                           (SEQ ID NO: 5)
5'-GGGGATATCCACCATGG(A or G)ATG(C or G)AGCTG(T or
G)GT(C or A)AT(C or G)CTCTT-3'

Reverse
                                           (SEQ ID NO: 6)
5'-AGGTCTAGAA(C or T)CTCCACACACAGG(A or G)(A or
G)CCAGTGGATAGAC-3'

2nd PCR Primers
Forward
                                           (SEQ ID NO: 7)
5'-GGGGATATCCACCATGGAATGGAGCTGGGTAATCCTCTT-3'

Reverse
                                           (SEQ ID NO: 8)
5'-GGTGTTGTGCTAGCTGAGGAGACTGTGA-3'

Light Chain
1st PCR Primers
Forward
                                           (SEQ ID NO: 9)
5'-GGGGATATCCACCATGGATTTTCAGGTGCAGATTTTCAG-3'

Reverse
                                           (SEQ ID NO: 10)
5'-GCGTCTAGAACTGGATGGTGGGAAGATGG-3'

2nd PCR Primers
Forward
                                           (SEQ ID NO: 9)
5'-GGGGATATCCACCATGGATTTTCAGGTGCAGATTTTCAG-3'

Reverse
                                           (SEQ ID NO: 11)
5'-AGCGTCGACTTACGTTTCAGCTCCAGCTTGGTCCC-3'
```

For production of the aCD20 component, the heavy and light chain fragments were cloned into a hIgG3 heavy chain expression vector (pAH 464) and a kappa (κ) light chain expression vector (pAH 462), respectively, (pAH 464 and pAH 462 were kindly provided by Dr. Joseph Rosenblatt at University of Miami) resulting in anti-CD20-immunoglobulin G3 (anti-CD20-IgG3) for expression in sp2/0 hybridoma cells.

For expression in Chinese Hamster Ovary (CHO) cells, the heavy chain and light chain fragments were cloned into pAH 6180 and pAN 6714 vectors, respectively (pAH 6180 and pAN 6714 vectors were provided as a gift by Dr. Sherie Morrision at UCLA). For the construction of the αCD20-hIL-21 fusokine, the IL-21 sequence was cloned into a pcDNA 3.1 vector. Due to the lack of sufficient data on the potential effects on the folding and efficacy of fusion proteins, various constructs were made.

Figure 2:
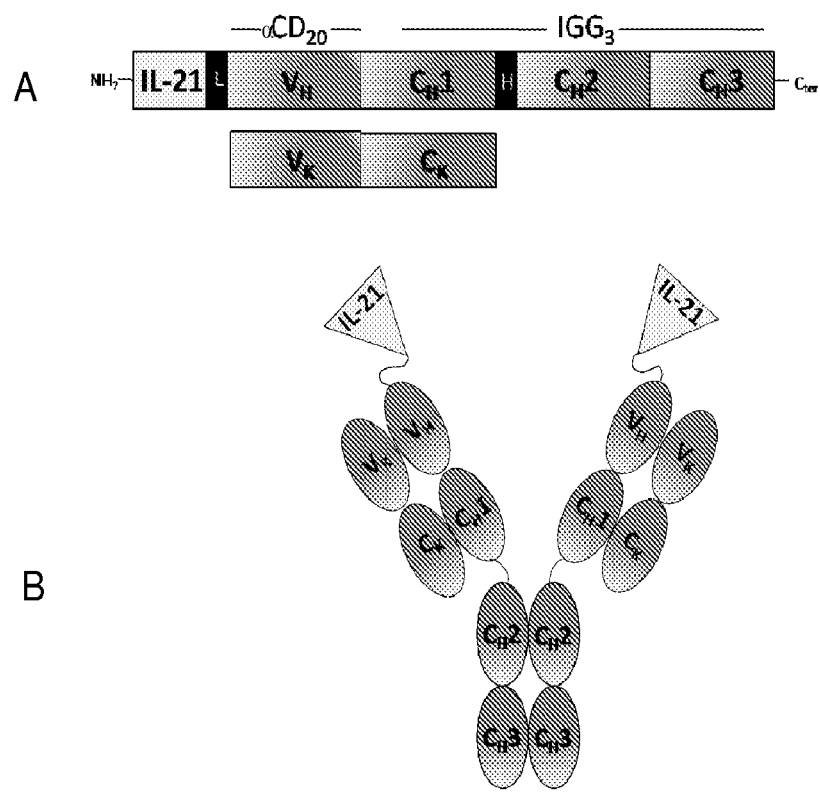
FIG. 2 shows a schematic representation of an embodiment of the present invention comprising a model of an expression cassette (A) and structure (B) of the anti-CD20-IL-21 fusion protein with the IL-21 component fused to the amino-terminal end of the CD20 antibody component via a linker peptide (collectively referred herein as "αCD20-N.IL21"). $V_H$ and $V_K$ indicate the variable region of the anti-CD20 component. "$C_H1$," "$C_H2$," and "$C_H3$" represent the human $\gamma_3$ heavy chain. "L" represents an $(SGGGG)_3$ (SEQ ID NO:1) linker between the IL-21 component and CD20 antibody component. "H" represents the hinge region of the antibody component.

In one construct, IL-21 sequence was fused to the amino-terminal (i.e., N-terminal) portion of the αCD20-IgG3, as depicted schematically in FIG. 1, using the IL-21 DNA sequence of SEQ ID NO:12. The subcloned hIL-21 gene was ligated to the $NH_2$ end of the αCD20-IgG3 expression vector using a 15 amino acid peptide linker (SGGGG)$_3$ (SEQ ID NO:1) at the end of the N-terminus to generate the fusion protein αCD20-N.IL-21 (FIG. 1). FIG. 2 depicts a schematic model of the corresponding expression cassette (A) and structure (B) of the αCD20-N.IL-21 fusion.

N-Terminal Fusion IL-21 DNA Sequence

```
                                         (SEQ ID NO: 12)
ccccaagcttgatatcgccaccATGAGATCCAGTCCTGGCAACATGGAGA

GGATTGTCATCTGTCTGATGGTCATCTTCTTGGGGACACTGGTCCACAAA

TCAAGCTCCCAAGGTCAAGATCGCCACATGATTAGAATGCGTCAACTTAT

AGATATTGTTGATCAGCTGAAAAATTATGTGAATGACTTGGTCCCTGAAT

TTCTGCCAGCTCCAGAAGATGTAGAGACAAACTGTGAGTGGTCAGCTTTT

TCCTGCTTTCAGAAGGCCCAACTAAAGTCAGCAAATACAGGAAACAATGA

AAGGATAATCAATGTATCAATTAAAAAGCTGAAGAGGAAACCACCTTCCA

CAAATGCAGGGAGAAGACAGAAACACAGACTAACATGCCCTTCATGTGAT

TCTTATGAGAAAAAACCACCCAAAGAGTTCCTAGAAAGATTCAAATCACT

TCTCCAAAAGATGATTCATCAGCATCTGTCCTCTAGAACACACGGAAGTG

AAGATTCC
```

Figure 3:
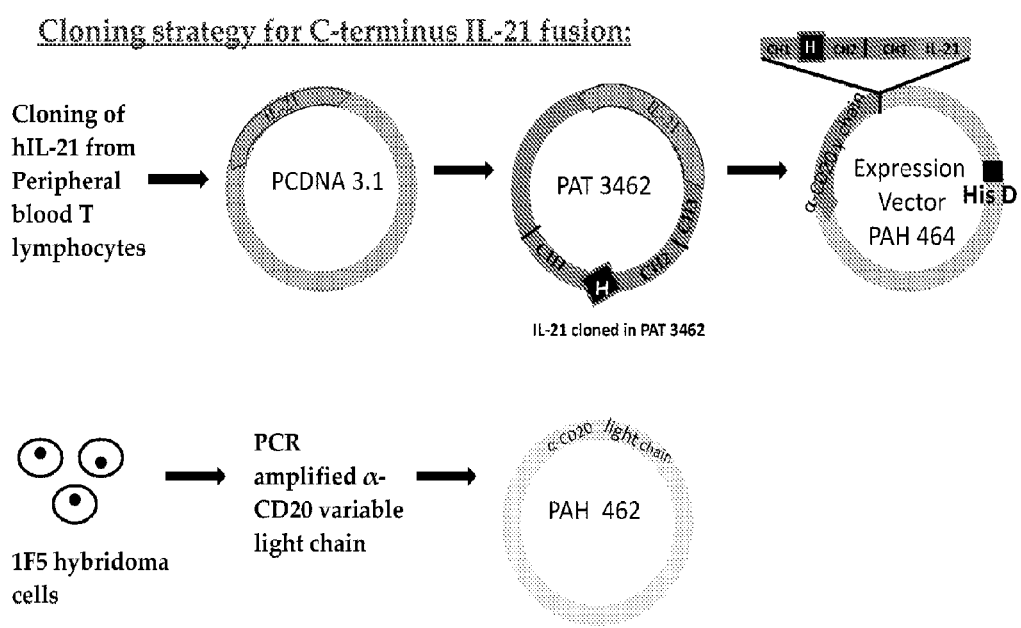
FIG. 3 shows a schematic representation of the present invention in an alternative embodiment comprising the cloning strategy for an anti-CD20-IL21 fusion protein with the IL-21 component fused to the carboxy-terminal end of the CD20 antibody component (referred herein as "αCD20-C.IL21"). "$C_H1$," "$C_H2$," and "$C_H3$" represent the human $\gamma_3$ heavy chain. "H" represents the hinge region of the antibody component.
Figure 4:
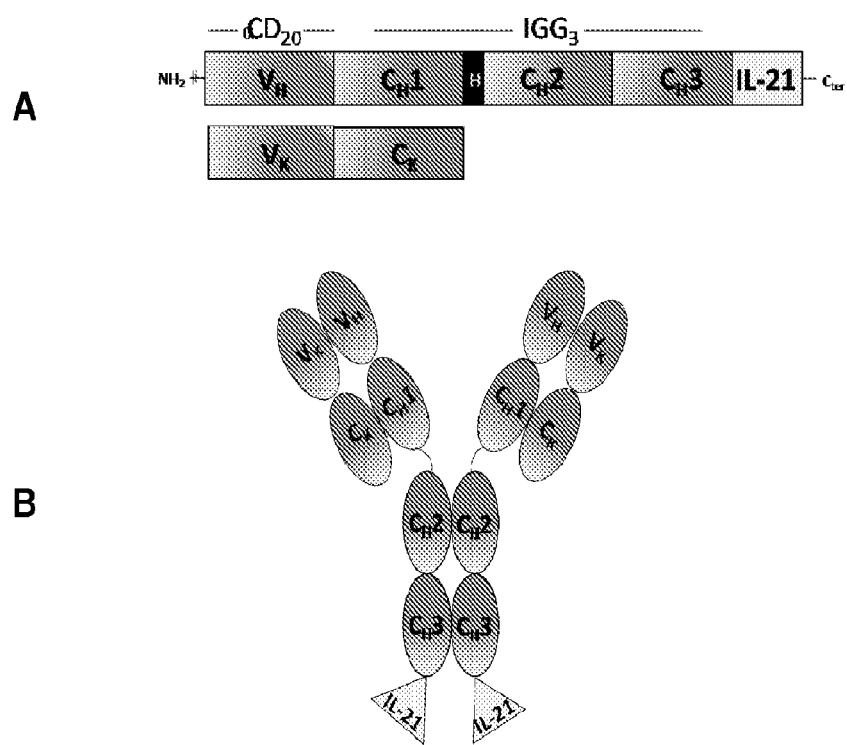
FIG. 4 shows a schematic representation of an embodiment of the present invention comprising a model of an expression cassette (A) and structure (B) of the anti-CD20-IL21 fusion protein with the IL-21 component fused to the carboxy-terminal end of the CD20 antibody component (referred herein as "αCD20-C.IL21"). $V_H$ and $V_K$ indicate the variable region of the anti-CD20 component. "$C_H1$," "$C_H2$," and "$C_H3$" represent the human $\gamma_3$ heavy chain. "H" represents the hinge region of the antibody component.

In another construct, IL-21 sequence was fused to the carboxy-terminal (i.e., C-terminal) portion of the αCD20-IgG3, depicted schematically in FIG. 3, using the IL-21 DNA sequence of SEQ ID NO:13. The subcloned hIL-21 gene was ligated directly to the $C_H3$ domain of αCD20-hIgG3, without a linker, to generate the fusion protein αCD20-C.IL-21 (FIG. 3). FIG. 4 depicts a schematic model of the corresponding expression cassette (A) and structure (B) of the αCD20-C.IL-21 fusion.

C-Terminal Fusion IL-21 DNA Sequence

```
                                         (SEQ ID NO: 13)
GGGGGAGCTCAAGATCGCCACATGATTAGAATGCGTCAACTTATAGATAT

TGTTGATCAGCTGAAAAATTATGTGAATGACTTGGTCCCTGAATTTCTGC

CAGCTCCAGAAGATGTAGAGACAAACTGTGAGTGGTCAGCTTTTTCCTGC

TTTCAGAAGGCCCAACTAAAGTCAGCAAATACAGGAAACAATGAAAGGAT

AATCAATGTATCAATTAAAAAGCTGAAGAGGAAACCACCTTCCACAAATG

CAGGGAGAAGACAGAAACACAGACTAACATGCCCTTCATGTGATTCTTAT

GAGAAAAAACCACCCAAAGAGTTCCTAGAAAGATTCAAATCACTTCTCCA

AAAGATGATTCATCAGCATCTGTCCTCTAGAACACACGGAAGTGAAGATT

CCGGTTAACGAATTCGGGG
```

Example 2

Characterization of αCD20-IL-21 Fusokines

Figure 5:
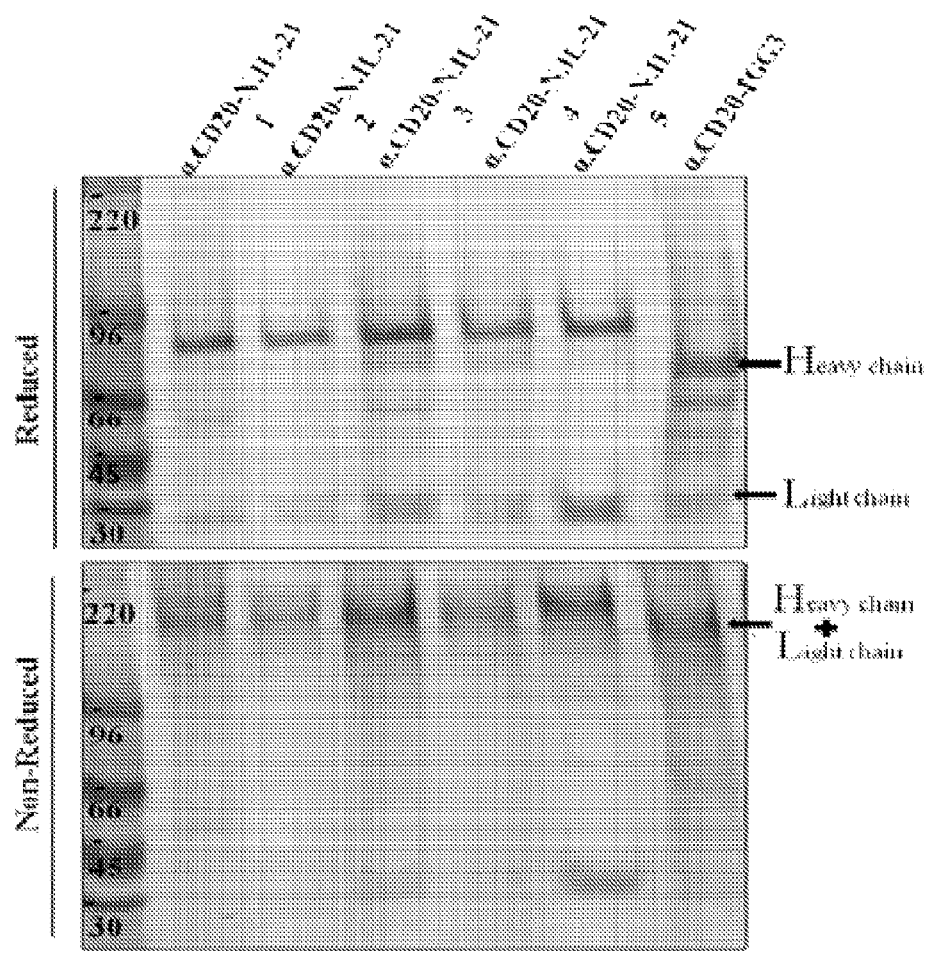
FIG. 5 shows an SDS-PAGE analysis of $^{35}S$ labeled αCD20-N.IL21 fusion protein. Fusion protein transfectomas labeled with $^{35}S$ were subjected to SDS-PAGE analysis under reduced (top panel) and non-reduced (bottom panel) conditions. Detection of αCD20-N.IL21 clones is shown in lanes 1 through 5 and detection of αCD20-IgG3 is shown in lane 6.

To confirm the correct size and structure of the expressed fusokines, [$^{35}$S]-methionine labeling was performed, followed by immunoprecipitation with protein G beads (FIG. 5) and MASS spectroscopy/protein sequencing (not shown). sp2/0 cells transfected with the fusion construct were metabolically labeled with [$^{35}$S]-methionine overnight. The supernatant containing the secreted fusion protein was collected and immunoprecipitated with protein G beads (Invitrogen). Proteins bound by the beads were analyzed using reducing and non-reducing SDS-PAGE (FIG. 5). αCD20-N.IL-21 clones (lanes 1 through 5) are detected as expected. αCD20-IgG3 is detected as a control in lane 6.

Example 3

Purification of αCD20-IL-21 Fusokines

The vectors encoding fusokines were stably expressed in sp2/0 hybridoma and CHO cells expressing the αCD20 κ light chain. Transfected clones were screened using sandwich ELISA designed to detect αhIgG, H, and L chains. Colonies producing the highest levels of monoclonal antibodies (mAbs) were expanded and plated as single cells by limited dilution to derive mAbs. Supernatant collected from the highest producing clones were used for the subsequent preliminary experiments. CHO cells were used to produce large quantities of the fusokines.

Figure 6:
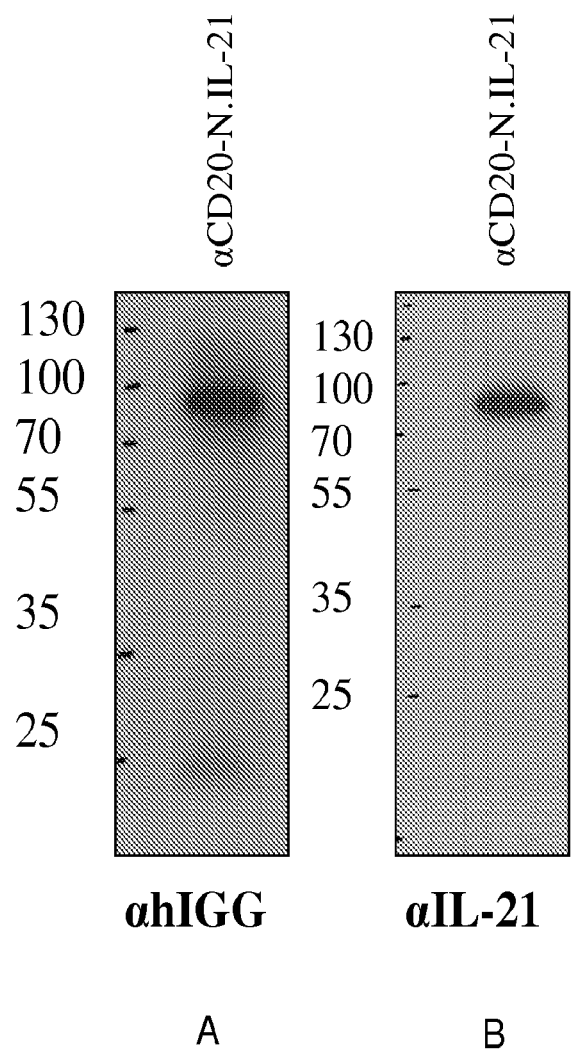
FIG. 6 shows fusion protein production in Chinese hamster ovary (CHO) cells by Western blot analysis. αCD20-N.IL21 is shown under reducing conditions detected by αhIGG (A) and αIL-21 (B) antibodies.

For purification of the fusion construct, the highest secreting clones of αCD20-IL21 and control αCD20-IgG3 were cultured in roller bottles and supernatant was passed through a Sepharose G fast flow column (GE Health Care) and the bound protein was eluted using 0.1M glycine pH 2.5. Eluted fractions were analyzed using western blotting to verify protein size, purity and integrity. As shown, western blotting for αhIgG (FIG. 6A) and αIL-21 (FIG. 6B) verify that the αCD20-N.IL-21 fusion protein is of the appropriate size and integrity. The expected molecular weight of the fusion protein is about 88 KDa.

Furthermore, the resulting amino acid sequence of the fusion protein obtained is shown in SEQ ID NO:14.

αCD20-N.IL-21 Fusion Protein Amino Acid Sequence

```
                                         (SEQ ID NO: 14)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDSSGGGGSGGGGSGGGGMA

QVQLRQPGAELVKPGASVKMSCKASGYTFTSYNMHWVKQTPGQGLEWIGA

IYPGNGDTSYNQKFKGKATLTADKSSSTAYMQLSSLTSEDSAVYYCARSH

YGSNYVDYFDYWGQGTSASAlaSerThrLysGlyProSerValPhePro

LeuAlaProCysSerArgSerThrSerGlyGlyThrAlaAlaLeuGly

CysLeuValLysAspTyrPheProGluProValThrValSerTrpAsn

SerGlyAlaLeuThrSerGlyValHisThrPheProAlaValLeuGln

SerSerGlyLeuTyrSerLeuSerSerValValThrValProSerSer

SerLeuGlyThrGlnThrTyrThrCysAsnValAsnHisLysProSer
```

-continued

```
AsnThrLysValAspLysArgValGluLeuLysThrProLeuGlyAsp

ThrThrHisThrCysProArgCysProGluProLysSerCysAspThr

ProProProCysProArgCysProGluProLysSerCysAspThrPro

ProProCysProArgCysProGluProLysSerCysAspThrProPro

ProCysProArgCysProAlaProGluLeuLeuGlyGlyProSerVal

PheLeuPheProProLysProLysAspThrLeuMetIleSerArgThr

ProGluValThrCysValValValAspValSerHisGluAspProGlu

ValGlnPheLysTrpTyrValAspGlyValGluValHisAsnAlaLys

ThrLysLeuArgGluGluGlnTyrAsnSerThrPheArgValValSer

ValLeuThrValLeuHisGlnAspTrpLeuAsnGlyLysGluTyrLys

CysLysValSerAsnLysAlaLeuProAlaProIleGluLysThrIle

SerLysAlaLysGlyGlnProArgGluProGlnValTyrThrLeuPro

ProSerArgGluGluMetThrLysAsnGlnValSerLeuThrCysLeu

ValLysGlyPheTyrProSerAspIleAlaValGluTrpGluSerAsn

GlyGlnProGluAsnAsnTyrAsnThrThrProProMetLeuAspSer

AspGlySerPhePheLeuTyrSerLysLeuThrValAspLysSerArg

TrpGlnGlnGlyAsnIlePheSerCysSerValMetHisGluAlaLeu

HisAsnArgTyrThrGlnLysSerLeuSerLeuSerProGlyLys.
```

Example 4

αCD20-IL-21 Fusokines Retain Specific Binding Ability to CD20

Figure 7:
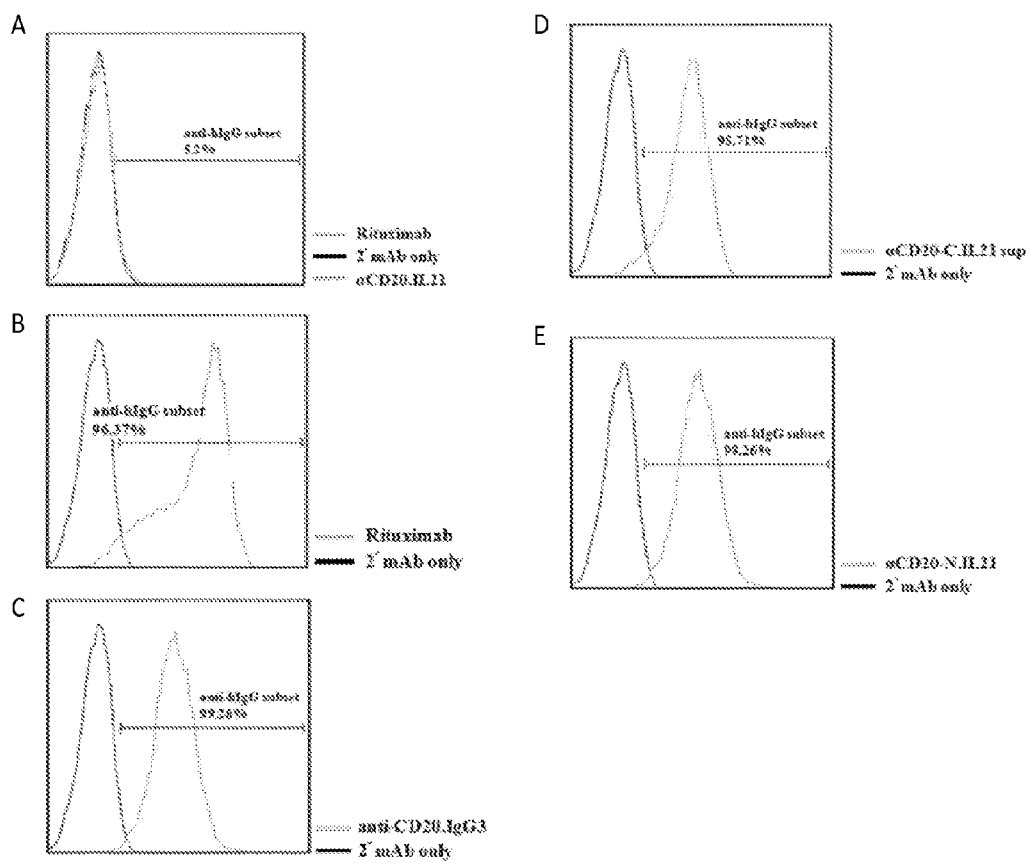
FIG. 7 shows cytometric analysis of binding of the αCD20-IL-21 fusokines to 38c13-huCD20 and 38c13 cells. Cells were incubated with indicated fusion protein supernatants or purified fusion proteins followed by staining with anti-hIGG-FITC. Black lines indicate background fluorescence obtained from staining of cells with secondary monoclonal antibody (anti-hIgG-FITC) only.

To examine the ability and specificity of αCD20-IL-21 fusokine binding to CD20, murine B cell lymphoma cell line 38c13 stably transfected with human CD20 (38c13-huCD20) (kindly provided by Josee Golay, Italy) and parental cell line 38c13 were used. Flow cytometry data demonstrated positive binding of N- and C-terminal αCD20-IL-21 fusokines in 38c13-huCD20 cells. C-terminal αCD20-IL-21 binding is shown in 38c13-huCD20 cells in FIG. 7d and N-terminal αCD20-IL-21 binding is shown in FIG. 7e. Parental 38c13 cells (FIG. 7a) show no fusion protein or rituximab binding. However, rituximab (FIG. 7b) and anti-CD20.IgG3 (FIG. 7c) binding is confirmed in the 38c13-huCD20 cells. It should be noted that similar binding efficacy to CD20 was observed for the αCD20-IL-21 fusokines and parental αCD20-IgG3 antibody, as well for rituximab (a commercially available chimeric monoclonal antibody against CD20). These data suggest that fusion of IL-21 to the αCD20 mAb does not interfere with the antibody binding to CD20.

Figure 8:
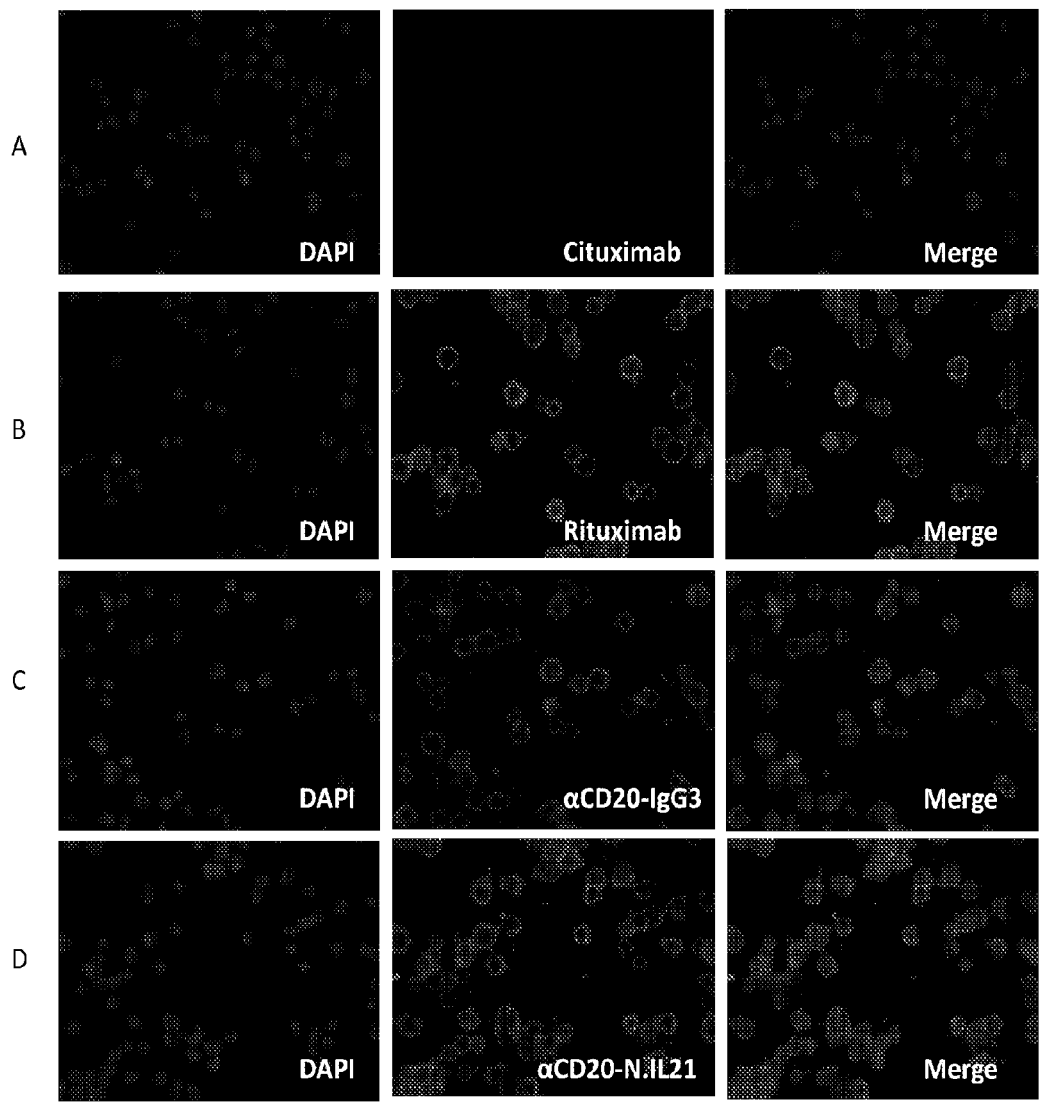
FIG. 8 shows immunofluorescence analysis of CD20 expressing Raji cells incubated with either cituximab (A), rituximab (B), αCD20-IgG3 (C), or αCD20-N.IL21 (D) as the 1° antibody, and αhIgG-Alexa fluor as the 2° antibody. Panels on the left show nuclei staining with DAPI, central panels show antibody expression, and panels on the right show a merge of antibody and DAPI staining. Images were taken at 400× magnification.

The ability of the αCD20-IL-21 fusokine to bind CD20 was confirmed by immunofluorescence. Specifically, $1 \times 10^5$ Raji cells (CD20 expressing B-cell lymphomas) were cytospun at 800 rpm for 3 minutes. The Raji cells were then coated with and incubated in either cituximab (anti-EGFR antibody), rituximab (anti-CD20 antibody), anti-CD20-IgG3 and anti-CD20-N.IL21 antibody, at antibody concentrations of 1 µg/ml. Following incubation, the cells were treated with immunofluorescence staining with anti-IgG-Alexa flour 647 ($2^{nd}$ antibody) and analyzed by immunofluorescence analysis according to standard protocol from Invitrogen. Nuclei were stained with DAPI, and cells were visualized by immunofluorescence microscopy at 400× magnification. The results of these experiments, presented in FIG. 8, show that the αCD20-N.IL21 fusokine (FIG. 8D) binds CD20 as well as or better than the positive control rituximab (FIG. 8B) or another CD20 fusion protein, CD20-IgG3 (FIG. 8C). As expected, the negative control cituximab (FIG. 8A) shows no binding to CD20.

Example 5

αCD20-IL-21 Fusokines Retain Specific Binding Ability to IL-21R

Figure 9:
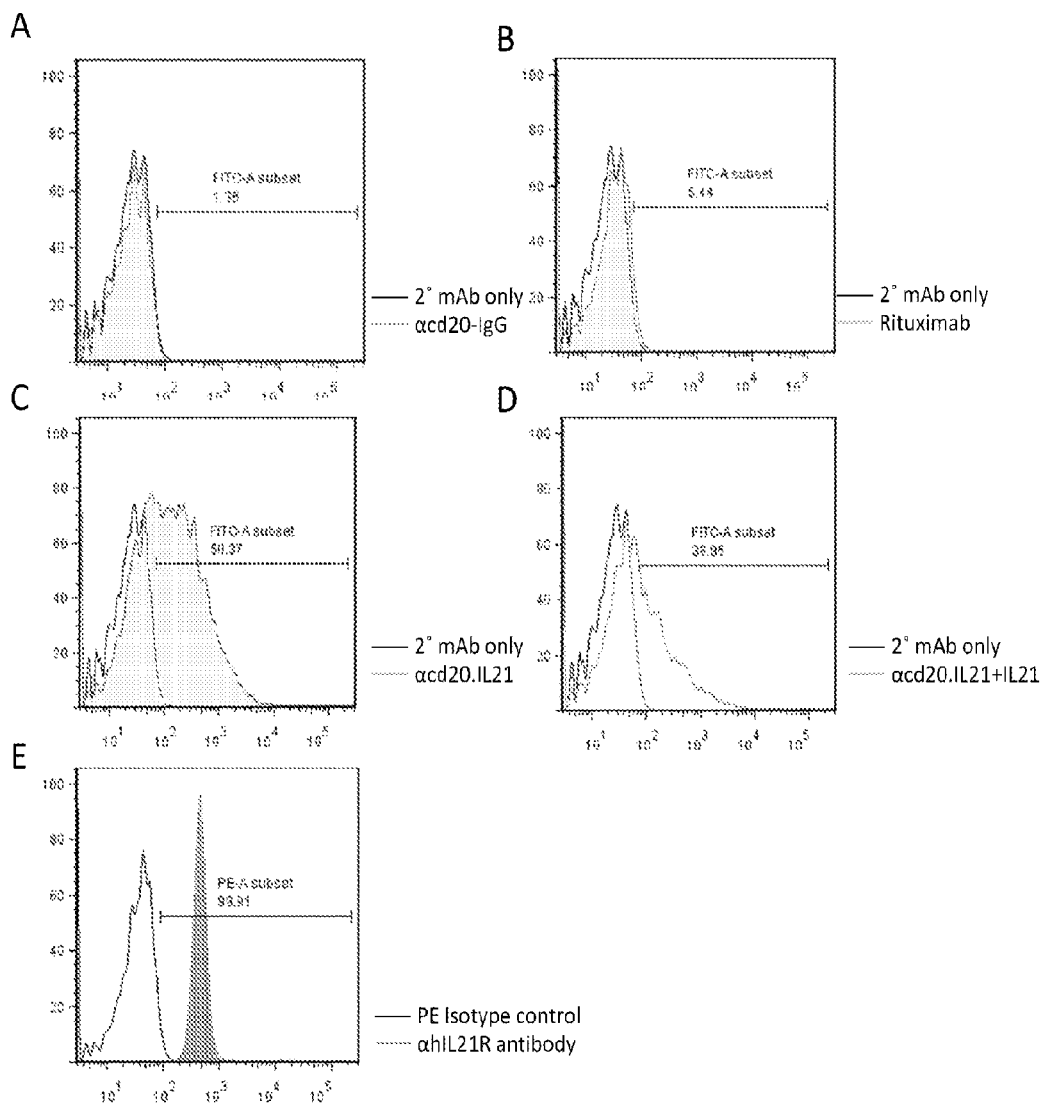
FIG. 9 shows flow cytometry histograms of IL-21R overexpressing YB2/0 cells incubated with either αCD20-IgG (A), rituximab (B), αCD20.IL21 (C), αCD20.IL21+IL21 (D), or αhIL21R (E) as the 1° antibody, followed by αhIgG-FITC as the 2° antibody for panels A-D and PE as the 2° antibody for panel E. In all histograms, X-axis shows fluorescence intensity and Y-axis represents cell count. Number of positive cells in each panel is described on the top of each gate.

To analyze the αCD20-IL-21 fusokine ability to bind to IL-21R receptor, YB2/0 cells overexpressing m-IL21R (kindly provided by Thomas Malek of the University of Miami) were used. Approximately $0.1 \times 10^6$ YB2/0 cells were resuspended in cold staining buffer containing 2% FBS, and 1 mg/ml FcγII/III blocker and incubated for 15 minutes. YB2/0 cells were then incubated with one of αCD20-IgG, rituximab (αCD20), αCD20.IL21 or αCD20.IL21+IL21 for 1 hour, followed by staining with anti-hIgG-FITC ($2^{nd}$ antibody) for 30 minutes. Cells were analyzed by flow cytometry on a BD FACS Canto Analyzer (BD Biosciences). The resulting histograms show binding of αCD20-IgG3 (FIG. 9A), Rituximab (FIG. 9B), αCD20.IL21 (FIG. 9C), αCD20.IL21+IL21 (FIG. 9D), and αhIL21R antibody (FIG. 9E). In each, the X-axis shows fluorescence intensity and Y-axis represents cell count, with the number of positive cells in each panel described on the top of each gate.

In addition, the ability of the αCD20-IL-21 fusokine to bind IL-21R was confirmed by immunofluorescence. Specifically, $1 \times 10^5$ YB2/0 cells (hybridoma cells overexpressing m-IL21R) were cytospun at 800 rpm for 3 minutes. YB2/0 cells were then coated with and incubated in either rituximab (anti-CD20 antibody), αCD20-IgG3 and αCD20-N.IL21 antibody, followed by capture using anti.IgG-Alexa fluor ($2^{nd}$ antibody), and analyzed by immunofluorescence analysis according to standard protocol from Invitrogen. Nuclei were stained with DAPI, and cells were visualized by immunofluorescence microscopy at 400× magnification.

Figure 10:
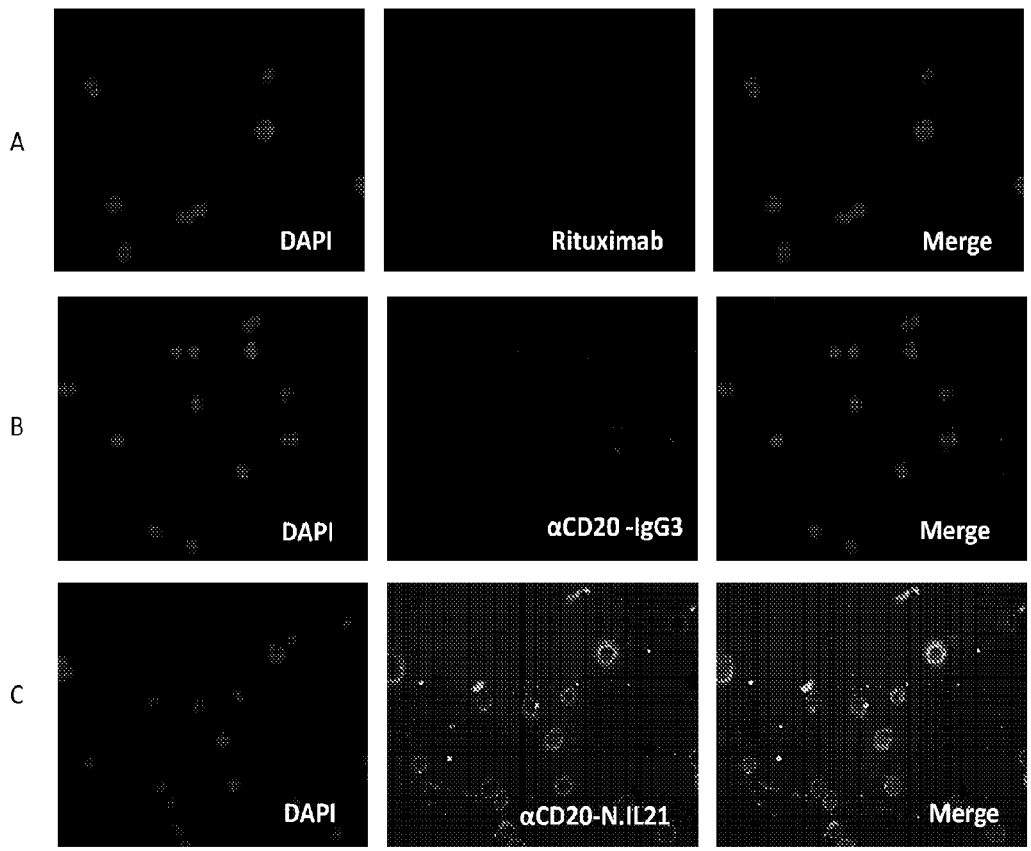
FIG. 10 shows immunofluorescence analysis of IL21R overexpressing YB2/0 cells incubated with either rituximab (A), αCD20-IgG3 (B), or αCD20-N.IL21 (C) as the 1° antibody, and αhIgG-FITC as the 2° antibody. Panels on the left show nuclei staining with DAPI, central panels show antibody expression, and panels on the right show a merge of antibody and DAPI staining. Images were taken at 400× magnification.

The results of these experiments, presented in FIG. 10, show that αCD20-N.IL21 fusokine (FIG. 10C) does indeed bind IL-21R receptor. This is due to the IL-21 component of the fusokine, neither αCD20-IgG3 (FIG. 10B) nor negative control rituximab (FIG. 10A) show binding. Moreover, this confirms that the fusion of αCD20 antibody with IL-21 cytokine does not impair IL-21 binding ability.

Figure 11:
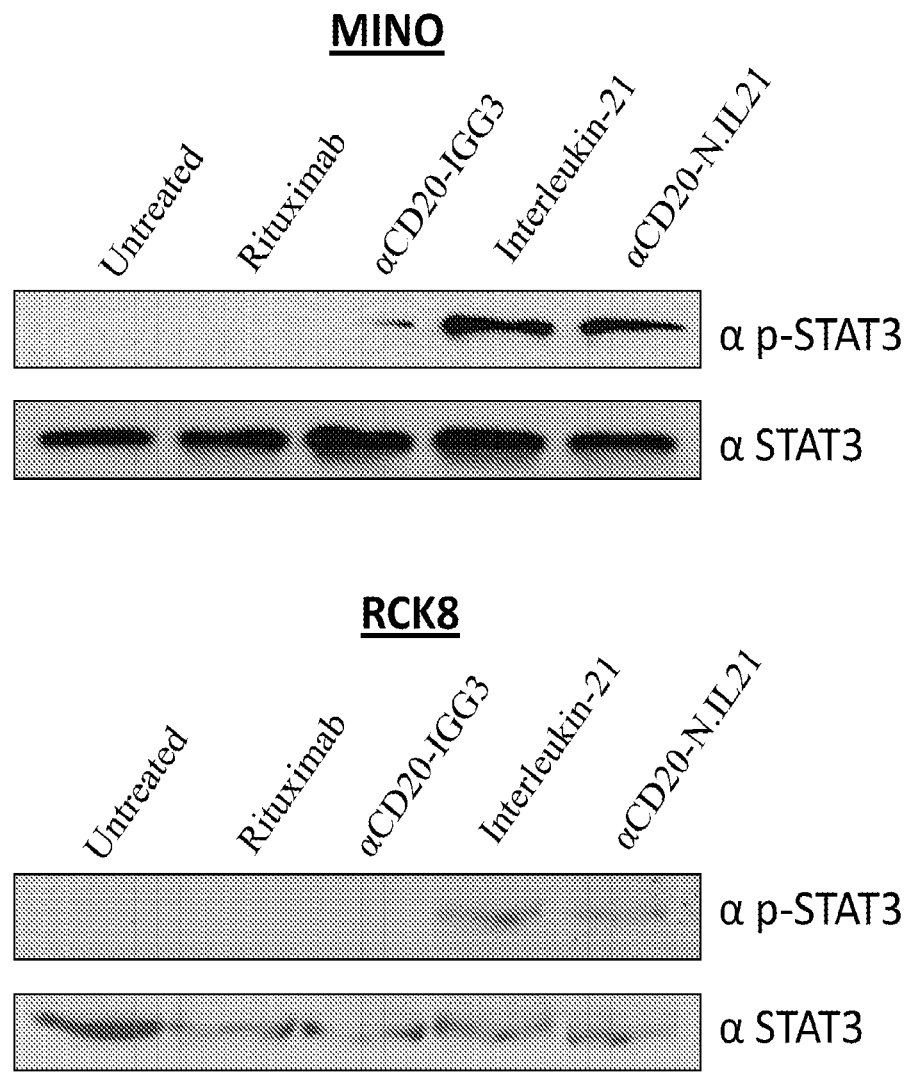
FIG. 11 shows immunoblotting of phosphorylated STAT3 (pSTAT3) and STAT3 (a normalizing control) in Mino cell lysates (A) and RCK8 cell lysates (B). Blotting of lysates is depicted from untreated, Rituximab treated, αCD20-IGG3 treated, Interleukin-21 treated, and αCD20-N.IL21 treated cells (shown in lanes from left to right, respectively).

Finally, the fusokine's IL-21 cytokine functionality was determined by testing its ability to induce STAT5 phosphorylation. To this end, Mino mantle cell lymphoma (MCL) and RCK8 cells, which express high levels of IL-21R, were stimulated for 30 minutes with supernatant containing either rituximab, αCD20-IgG3, IL-21, or N-terminal αCD20-IL-21 fusokine, as indicated in FIG. 11. Proteins were subsequently extracted from whole cell lysates, and phosphorylated STAT3 (pSTAT3) levels were examined by Western blot analysis, with total STAT3 levels utilized as the normalizing control. As is evident from FIG. 11, STAT3 was phosphorylated upon treatment with N-terminal αCD20-IL-21 fusokine (αCD20-N.IL21), but not with the αCD20-IgG3 control or the αCD20 antibody rituximab. This expression pattern was seen in both Mino cells (FIG. 11A) and RCK8 cells (FIG. 11B), to a lesser degree. As expected, and as a positive control, treatment with IL-21 resulted in phosphorylation of STAT3. Furthermore, untreated cells exhibited no STAT3 phosphorylation. These data demonstrate that the fusokine of the present invention can activate an IL-21R signaling cascade similar to IL-21, and, as expected, αCD20 mAb (rituximab) alone elicits no such activation of the IL-21R signaling cascade. This signaling cascade is therefore IL-21 dependent, and indicates the IL-21 portion of the fusokine of the present invention is active and functional.

Example 6

αCD20-IL-21 Fusokine Induces Apoptosis of B-Cell Lymphomas

Figure 12:
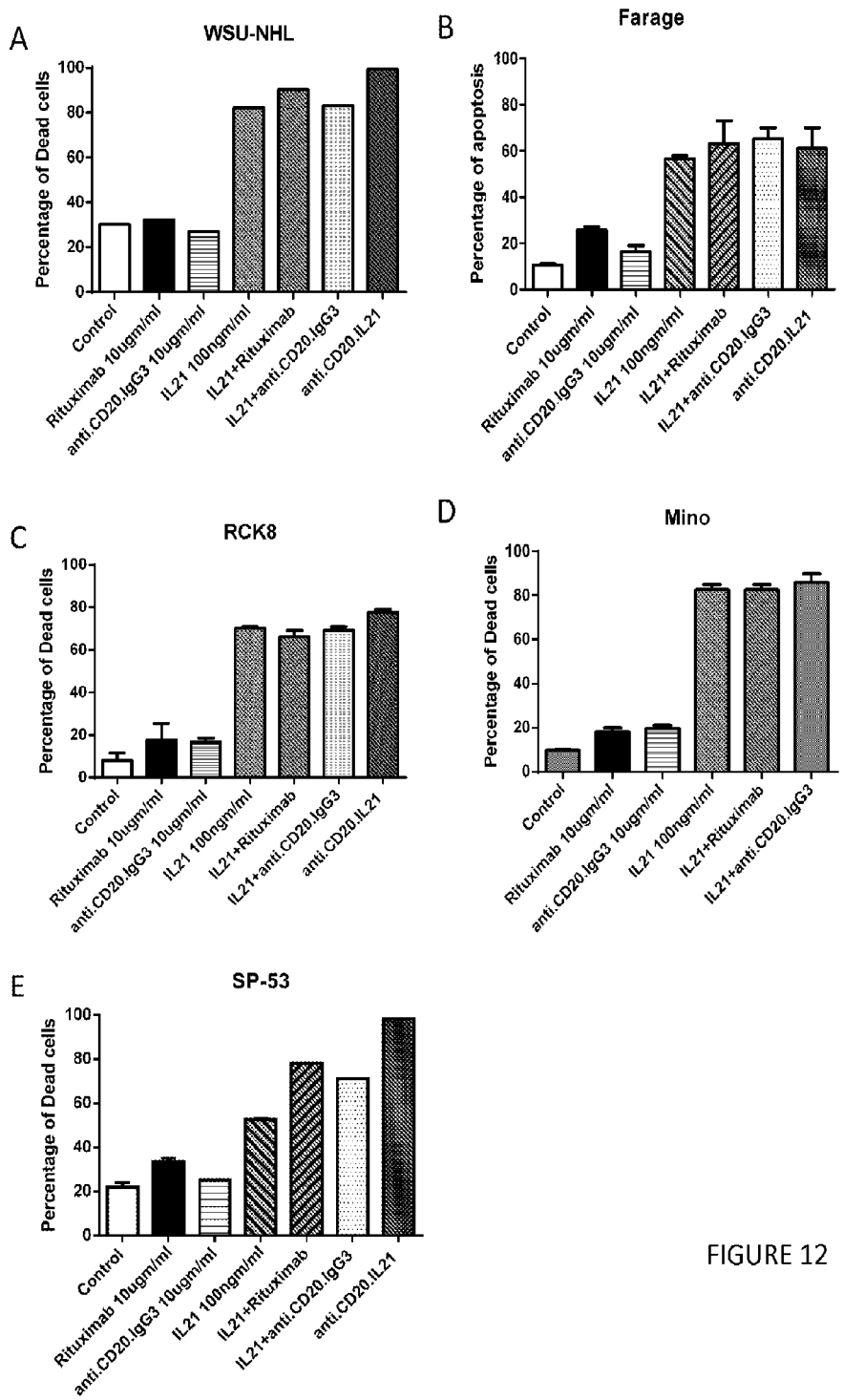
FIG. 12 shows apoptotic levels in WSU-NHL cells (A), Farage cells (B), RCK8 cells (C), Mino cells (D), and SP-53 cells (E) incubated with various treatments for 72 hours. Cells were treated with the indicated treatments for 72 hours (A-D) or 120 hours (E), followed by staining with YO-PRO-1 and PI to determine levels of cell death by flow cytometric analysis. Cells positive for both dyes are characterized as apoptotic (dead) cells. Fold change in percentage of cell death is shown. Error bars represent standard error of mean.

To evaluate the therapeutic potential of the αCD20-IL-21 fusokine in B-cell lymphomas, the ability of the fusokine to induce direct cytotoxicity in the following lymphoma cell lines was analyzed: WSU-NHL, Farage, RCK8 DLBCL, Mino mantle cell lymphoma (MCL), and SP-53. To this end, purified protein from the N-terminal fusion construct was incubated with the indicated cells for 72 hours for WSU-NHL, Farage, RCK8, and Mino cells, or 120 hours for SP-53 cells. Cells were analyzed for apoptosis and death by YO-PRO-1 (Invitrogen) and propidium iodide (Invitrogen) staining (FIG. 12). Flow cytometric analysis revealed that higher levels of apoptosis and cell death were achieved with the fusokine compared to IL-21 alone or in combination with the parental antibody (IL-21+αCD20-IgG3) in all the tested lymphoma cell lines, specifically, WSU-NHL cells (FIG. 12A), Farage (FIG. 12B), RCK8 (FIG. 12C), Mino (FIG. 12D), and SP-53 (FIG. 12E) cells. As expected, in the absence of effector cells, rituximab and αCD20-IgG3 parental antibodies exerted minimal direct cytotoxicity. Of note, based on experience and as previously reported, maximal IL-21 effects are observed at a dose of 100 ng/mL used in the presented experiments. (Sarosiek et al. 2010). Consequently, the increase in cell apoptosis above the levels achieved with the 100 ng/mL of IL-21 can only be attributed to synergism achieved by simultaneous stimulation of both IL-21R and CD20 by the fusokine and not by its individual components. Furthermore, these studies demonstrate a dose response to the N-terminal fusokine in the WSU-NHL, RCK8, and SP-53 cells tested. These results point to the potential therapeutic efficacy of the αCD20-IL-21 fusokines. Similar to the previously reported minimal IL-21 effect on normal B cells, in vitro treatment with αCD20-IL-21 fusokine in the absence of effector immune cells also did not induce B cell apoptosis. (Sarosiek et al. 2010).

Example 7

αCD20-IL-21 Fusokine Leads to Activation of NK Cells

Since cytokines play a large role in NK cell activation, and therefore immune response, the αCD20-IL-21 fusokine of the present invention was tested for its ability to do the same. Monoclonal antibody (mAb) mediated NK cell activation can be used as a measure of antibody-dependent cytotoxicity effects. Response of NK cells to mAb-coated targets is determined by phenotypic evaluation of NK cells. Therefore, NK-cell response to a specific antibody was determined by quantification of CD16 down-modulation, which is mediated via interaction between CD16 of NK cells and the Fc portion of the antibody and up-regulation of CD69. Freshly isolated NK cells from human peripheral blood were utilized as effector cells (E) and B-cell lymphoma line, Raji cells, as target cells (T). Effector and target cells were co-cultured for 24 hours at the ratio of 1:1 (E/T) in the presence of either rituximab (2 μg/ml), αCD20-IgG3 (2 μg/ml), αCD20-IgG3+IL21 (2 μg/ml), or αCD20-N.IL21 (2 μg/ml) antibodies or IL21 (100 ng/ml) or PBS (control). At the end of incubation, cells were stained for CD3, CD54, CD69 and CD16 cytokines, followed by flow-cytometry analysis of BD FACS Canto analyser.

Figure 13:
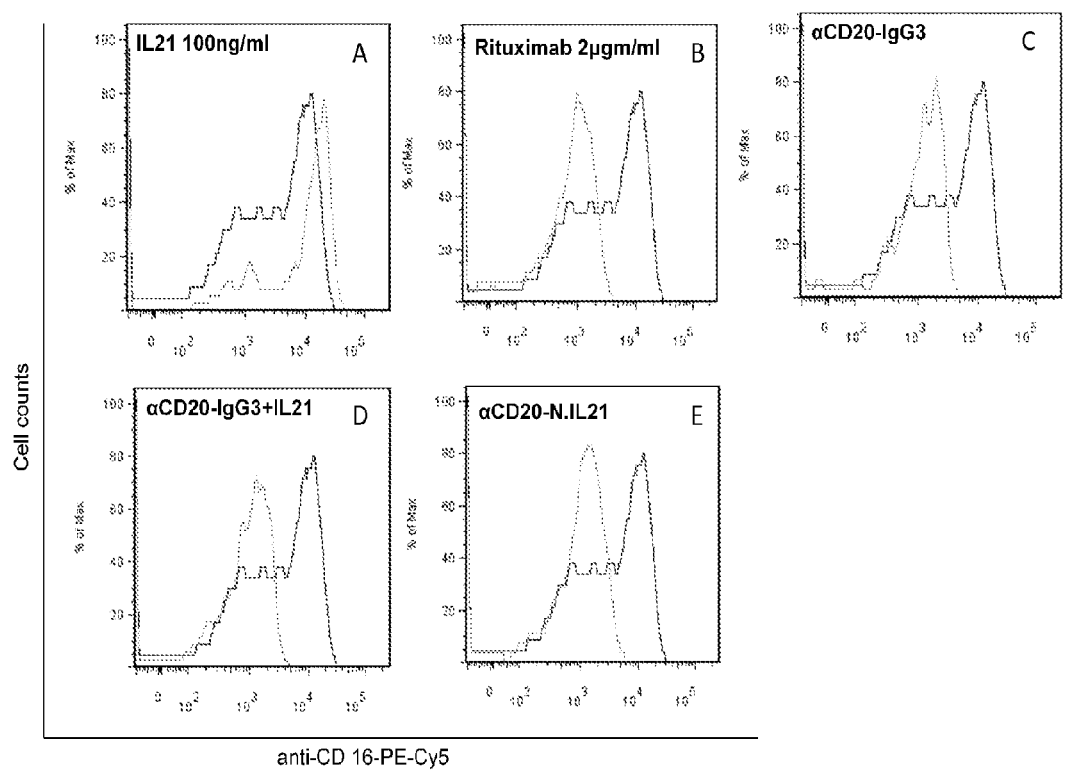
FIG. 13 shows flow cytometry histograms of freshly isolated human NK cells co-cultured with Raji cells at a ratio of 1:1 in the presence of either IL21 (A), rituximab (B), αCD20-IgG3 (C), αCD20-IgG3+IL21 (D), or αCD20-N.IL21 (E). CD16 expression was determined with gating on $CD3^-$ and $CD56^+$ NK cells. In all histograms, X-axis shows fluorescence intensity and Y-axis represents cell count. Histograms show PBS control in black lines and indicated antibodies in grey lines.

Expression of CD16 was determined by gating on CD3⁻ and CD56⁺ NK cells, shown in FIG. 13. In all histograms, X-axis shows fluorescence intensity and Y-axis represents cell count. Histograms for PBS control are indicated in black lines, and the indicated antibodies are represented in grey lines. As expected, negative control IL21 shows an upregulation of CD16 (FIG. 13A).

Downregulation of CD16 occured with αCD20-N.IL21 (FIG. 13E), as well as αCD20-IgG3+IL21 (FIG. 13D), αCD20-IgG3 (FIG. 13C), and positive control rituximab (FIG. 13B). As expected, negative control IL21 shows an upregulation of CD16 (FIG. 13A).

Figure 14:
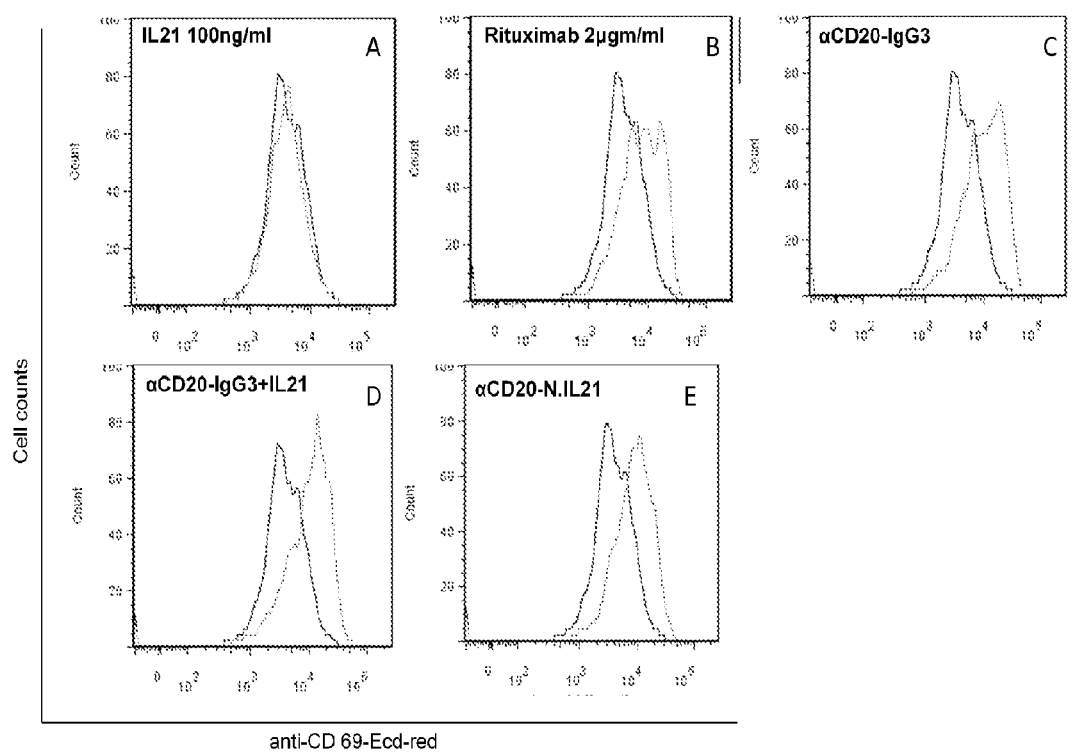
FIG. 14 shows flow cytometry histograms of freshly isolated human NK cells co-cultured with Raji cells at a ratio of 1:1 in the presence of either IL21 (A), rituximab (B), αCD20-IgG3 (C), αCD20-IgG3+IL21 (D), or αCD20-N.IL21 (E). CD69 expression was determined with gating on $CD3^-$ and $CD56^+$ NK cells. In all histograms, X-axis shows fluorescence intensity and Y-axis represents cell count. Histograms show PBS control in black lines and indicated antibodies in grey lines.

On the other hand, CD69 was upregulated with αCD20-N.IL21 (FIG. 14E), as well as αCD20-IgG3+IL21 (FIG. 14D), αCD20-IgG3 (FIG. 14C), and positive control rituximab (FIG. 14B), as compared to negative control IL21 (FIG. 14A). Taken together, these data indicate that the αCD20-IL-21 fusokine of the present invention activates NK cells, and could be used for cytotoxic effect.

Example 8

αCD20-IL-21 Fusokine Exhibits Antibody Dependent Cellular Cytotoxicity (ADCC) Acitivity CD20⁺ Raji cells (target cells) were labeled with $^{51}$Cr-sodium chromate, coated with indicated antibodies and incubated with human NK cells (effector cells) isolated from healthy donor peripheral blood mononuclear cells (PBMCs) at a target to effector ratio of 1:10 for 4 hours. Tumor cell lysis, and consequent levels of $^{51}$Cr released into supernatant, was quantified using a scintillation counter to determine percentage of cell lysis. Minimum and maximum release was determined by incubation of labeled target cells in culture media alone, or media supplemented with 0.1% Triton X-100 detergent. Percentage of total cell lysis was determined using the following formula: (sample-spontaneous/maximal-spontaneous)*100.

Figure 15:
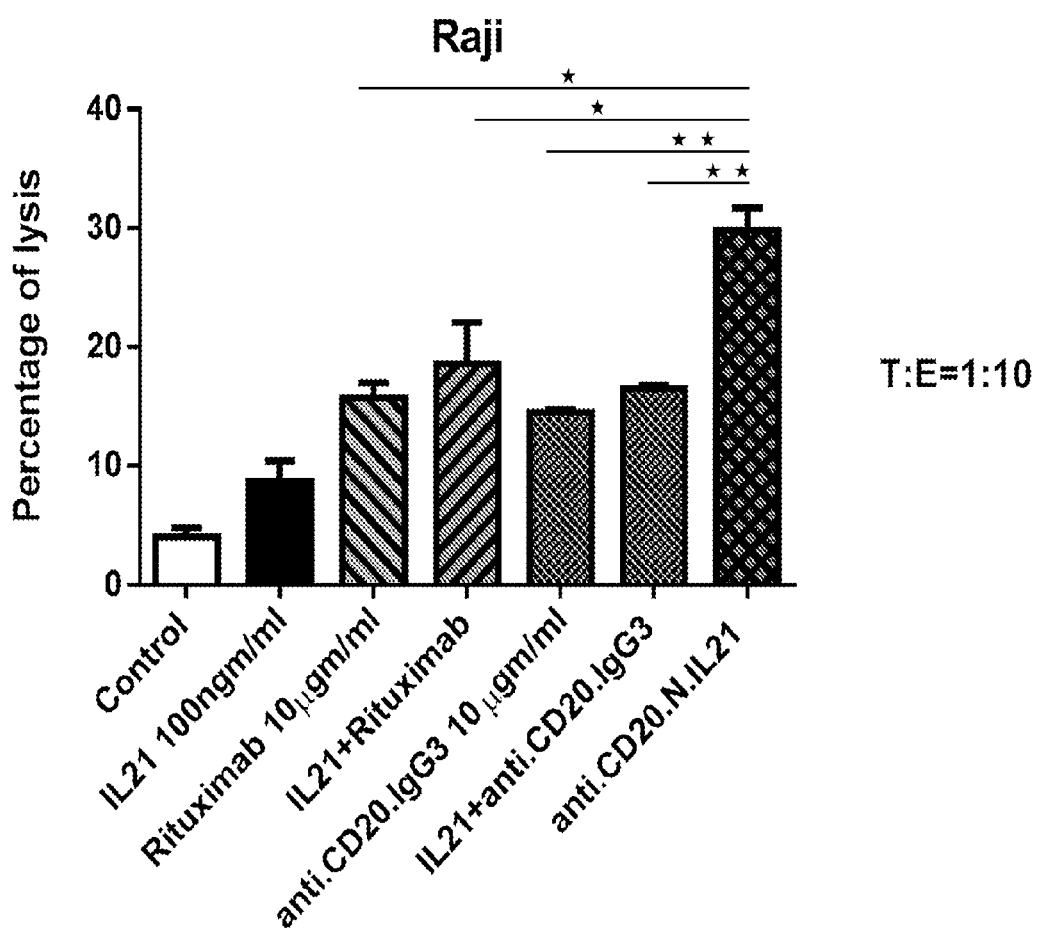
FIG. 15 shows a graphical representation of percentage of lysis of cells, as determined by scintillation counter. Raji cells (target cells) were labeled with $^{51}Cr$, followed by incubation with indicated antibodies. Human NK cells (effector cells) isolated from human peripheral blood were incubated at target to effector ratio of 1:10, and release of $^{51}Cr$ was measured using scintillation counter to determine percentage of cell lysis. Graphical bars represent percentage of cell lysis resulting from either control, IL21, rituximab, IL21+rituximab, anti.CD20.IgG3, IL21+anti.CD20.IgG3, or anti.CD20.N.IL21 (shown from left to right, respectively). Experiments were performed in triplicate, and error bars indicate mean+/−SD. *$P<0.05$. **$P<0.01$.

As seen in FIG. 15, cells incubated with αCD20-N.IL21 showed a statistically significant increase in the percentage of lysis and levels of $^{51}$Cr released, indicating a higher level of ADCC activity. Experiments were performed in triplicate, and error bars indicate mean+/−SD. *P<0.05. **P<0.01.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

The invention claimed is:

1. A recombinant fusion protein comprising an amino acid sequence of IL-21 or cytotoxic fragment thereof fused to an N-terminus of an amino acid sequence of an anti-CD20 antibody or antigen binding fragment thereof via a linker peptide of SEQ ID NO:1.

2. The fusion protein of claim 1 comprising an amino acid sequence as set forth in SEQ ID NO:14.

3. The fusion protein of claim 1 wherein the anti-CD20 antibody or antigen binding fragment thereof specifically binds one or more epitopes comprising the amino acid sequence set forth in SEQ ID NO:2 or SEQ ID NO:3, or combinations thereof.

4. The fusion protein of claim 1 wherein the anti-CD20 antibody or antigen binding fragment thereof specifically binds a polypeptide having an amino acid sequence as set forth in SEQ ID NO:4, or portions thereof.

5. The fusion protein of claim 1, wherein the anti-CD20 antibody is a monoclonal antibody.

6. The fusion protein of claim 1, wherein the antigen-binding fragment of the anti-CD20 antibody is selected from the group consisting of Fab, Fab', F(ab')2, Fv fragments, diabodies, single chain antibody molecules, and multispecific antibodies formed from antibody fragments.

7. The fusion protein of claim 1 further comprising a label.

8. The fusion protein of claim 7, wherein the label is a radiolabel.

9. An isolated polynucleotide comprising a nucleic acid sequence encoding the fusion protein of claim 1.

10. A cloning vector comprising the nucleotide sequence of claim 9.

11. An expression vector comprising the nucleotide sequence of claim 9.

12. An expression vector encoding the fusion protein of claim 1.

13. A cultured cell expressing the fusion protein of claim 1.

14. A pharmaceutical composition comprising the fusion protein of claim 1 and at least one pharmaceutically acceptable carrier.

15. The pharmaceutical composition of claim 14, further comprising one or more pharmaceutically acceptable excipient, additive, or adjuvant.

16. The pharmaceutical composition of claim 14 further comprising at least one of a chemotherapeutic agent, a radioactive isotope, a therapeutic agent, or combinations thereof.

17. A kit comprising the pharmaceutical composition of claim 14.

18. A method of treating CD20 expressing leukemia or lymphoma in a subject comprising administering a therapeutically effective amount of the fusion protein of claim 1 to the subject.

19. A method of treating an autoimmune disease in a subject comprising administering a therapeutically effective amount of the fusion protein of claim 1 to the subject, wherein the autoimmune disease is affected by modulation of natural killer (NK) cells, cytotoxic T cells or B-lymphocytes.

20. The method of claim 18 wherein the subject is a human.

21. The method of claim 18 further comprising administering to the subject a therapeutically effective amount of at least one agent selected from the group consisting of a chemotherapeutic agent, a radioactive isotope, a therapeutic agent, or combinations thereof.

22. The method of claim 18 wherein the fusion protein is administered with a pharmaceutically acceptable carrier.

23. A kit comprising the fusion protein of claim 1.

24. The kit of claim 23 further comprising at least one agent capable of facilitating detection of the fusion protein.

25. A method of targeted delivery to one or more CD20 expressing tumors in a subject comprising administering a therapeutically effective amount of the fusion protein of claim 1 to the subject.

26. The method of claim 25 further comprising activating one or more immune effector cells adjacent the one or more tumors by the recombinant fusion protein.

27. A method of inhibiting the growth of a CD20 expressing leukemia or lymphatic tumor cell comprising contacting the tumor cell with the fusion protein of claim 1.

28. A method of targeting CD20 and IL-21 receptors on a cell with a single protein, comprising contacting the cell with the fusion protein of claim 1.

29. A method of enhancing antibody dependent cellular cytotoxicity activity against CD20 expressing leukemia or lymphatic cells expressing CD20 in a subject comprising administering the fusion protein of claim 1 to the subject.

30. The method of claim 19 wherein the subject is a human.

31. The method of claim 19 further comprising administering to the subject a therapeutically effective amount of at least one agent selected from the group consisting of a chemotherapeutic agent, a radioactive isotope, a therapeutic agent, or combinations thereof.

32. The method of claim 19 wherein the fusion protein is administered with a pharmaceutically acceptable carrier.

* * * * *